US008546398B2

(12) United States Patent
Argade et al.

(10) Patent No.: US 8,546,398 B2
(45) Date of Patent: *Oct. 1, 2013

(54) STEREOISOMERICALLY ENRICHED 3-AMINOCARBONYL BICYCLOHEPTENE PYRIMIDINEDIAMINE COMPOUNDS AND THEIR USES

(75) Inventors: Ankush Argade, Foster City, CA (US); Rajinder Singh, Belmont, CA (US); Hui Li, Santa Clara, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 1461 days.

This patent is subject to a terminal disclaimer.

(21) Appl. No.: 11/280,066

(22) Filed: Nov. 15, 2005

(65) Prior Publication Data

US 2006/0167249 A1 Jul. 27, 2006

Related U.S. Application Data

(60) Provisional application No. 60/628,199, filed on Nov. 15, 2004.

(51) Int. Cl.
*C07D 239/48* (2006.01)
*A61K 31/506* (2006.01)

(52) U.S. Cl.
USPC ...................... 514/252.14; 544/295

(58) Field of Classification Search
USPC .................... 544/295; 514/252.14
See application file for complete search history.

(56) References Cited

U.S. PATENT DOCUMENTS

| | | | |
|---|---|---|---|
| 6,593,326 | B1 | 7/2003 | Bradbury et al. |
| 7,060,827 | B2 | 6/2006 | Singh et al. |
| 2004/0029902 | A1 | 2/2004 | Singh et al. |
| 2005/0113398 | A1 | 5/2005 | Argade et al. |
| 2005/0192301 | A1 | 9/2005 | Li et al. |
| 2005/0209224 | A1 | 9/2005 | Singh et al. |
| 2005/0209230 | A1 | 9/2005 | Singh et al. |
| 2005/0234049 | A1 | 10/2005 | Singh et al. |
| 2006/0025410 | A1 | 2/2006 | Singh et al. |
| 2006/0035891 | A1 | 2/2006 | Li et al. |
| 2006/0035916 | A1 | 2/2006 | Singh et al. |
| 2006/0040955 | A1 | 2/2006 | Singh et al. |
| 2006/0058292 | A1 | 3/2006 | Singh et al. |
| 2006/0058525 | A1 | 3/2006 | Singh et al. |
| 2006/0135543 | A1 | 6/2006 | Singh et al. |
| 2006/0166308 | A1 | 7/2006 | Argade |
| 2006/0167254 | A1 | 7/2006 | Cooper et al. |
| 2007/0179140 | A1 | 8/2007 | Argade et al. |
| 2007/0299060 | A1 | 12/2007 | Li et al. |
| 2008/0009494 | A1 | 1/2008 | Li et al. |

FOREIGN PATENT DOCUMENTS

| | | |
|---|---|---|
| WO | WO 00/03032 A1 | 1/2000 |
| WO | WO 02/059110 | 8/2002 |
| WO | WO 03/026664 | 4/2003 |
| WO | WO 03/030909 | 4/2003 |
| WO | WO 03/040141 | 5/2003 |
| WO | WO 2004/014382 A1 | 2/2004 |
| WO | 2005/063722 | 7/2005 |
| WO | WO 2005/118544 A2 | 12/2005 |
| WO | WO 2006/078846 A1 | 7/2006 |

OTHER PUBLICATIONS

Simone, Oncology: Introduction, Cecil Textbook of Medicind, 20th Editoin, vol. 1, pp. 1004-1010, 1996.*
Cuiper, Anne Dite, "Molecular Docking with *Candida antarctica* Lipase B[1]," *Enantioselective Synthesis of Lactams and Lactones: a Chemo-Enzymatic Approach*, Chapter 10, 1999, pp. 133-140, http://dissertations.ub.rug.nl/oai/.
Search Report from PCT/US05/ 041276 dated Jul. 12, 2006.
Search Report from GB0523012.3 dated Mar. 23, 2006.
Adam et al., 2000, "Synthesis of Optically Active α-Methylene β-Lactams Through Lipase-Catalyzed Kinetic Resolution," *J. Org. Chem.* 65:4919-4922.
Forro et al., 2004, "Direct and Indirect Enzymatic Methods for the Preparation of Enantiopure Cyclic β-Amino Acids and Derivatives from β-Lactams," *Mini-Reviews in Organic Chemistry*, 1(1):93-102.
Kurokawa et al., 2004, "Both Enantiomers of N-Boc-indoline-2-carboxylic Esters," *Bull. Chem. Soc. Jpn.* 77:1021-1025.
Parker et al., 1998, "Enhancement of *Candida antarctica* Lipase B Enantioselectivity and Activity in Organic Solvents," *Chem. Commun.* pp. 2247-2248.
Torre et al., 2004, "Lipase Catalysed Michael Addition of Secondary Amines to Acrylonitrile," *Chem. Commun.* pp. 1724-1725.
PCT International Search Report, Mar. 29, 2006.
Forro, et al. "Vapor-assisted enzymatic hydrolysis of beta-lactams in a solvent-fee system," Tetrahedron: Asymmetry, 2008, pp. 1005-1009, vol. 19, Elsevier, Oxford, United Kingdom.
Rogers, et al. "The aurora kinase AIR-2 functions in the release of chromosome cohesion in *Caenorhabditis elegans* meiosis," J Cell Biol., 2002, pp. 219-229.
Tanaka, et al., Evidence that the Ip11-Sli15 (Aurora kinase-INCENP) complex promotes chromosome bi-orientation by altering kinetochore-spindle pole connections, Cell, 2002, pp. 317-329.
Ulrich, Joachim, "Chapter 4: Crystallization," Kirk-Othmer Encyclopedia of Chemical Technology, Aug. 2002.
Vippagunta, et al., "Crystalline solids," Advanced Drug Delivery Reviews, 48, 2001, pp. 3-26.
West, Anthony, "Chapter 10: Solid Solutions," Solid State Chemistry and its applications, 2001, p. 358 and p. 365.

* cited by examiner

*Primary Examiner* — Deepak Rao
(74) *Attorney, Agent, or Firm* — Travis Young; McDonnell Boehnen Hulbert & Berghoff LLP

(57) ABSTRACT

The present invention provides stereoisomers and stereoisomeric mixtures of 3-aminocarbonyl-bicycloheptene-2,4-pyrimidinediamine compounds having antiproliferative activity, compositions comprising the compounds and methods of using the compounds to inhibit cellular proliferation and to treat proliferate diseases such as tumorigenic cancers.

3 Claims, 4 Drawing Sheets

Figure 1:
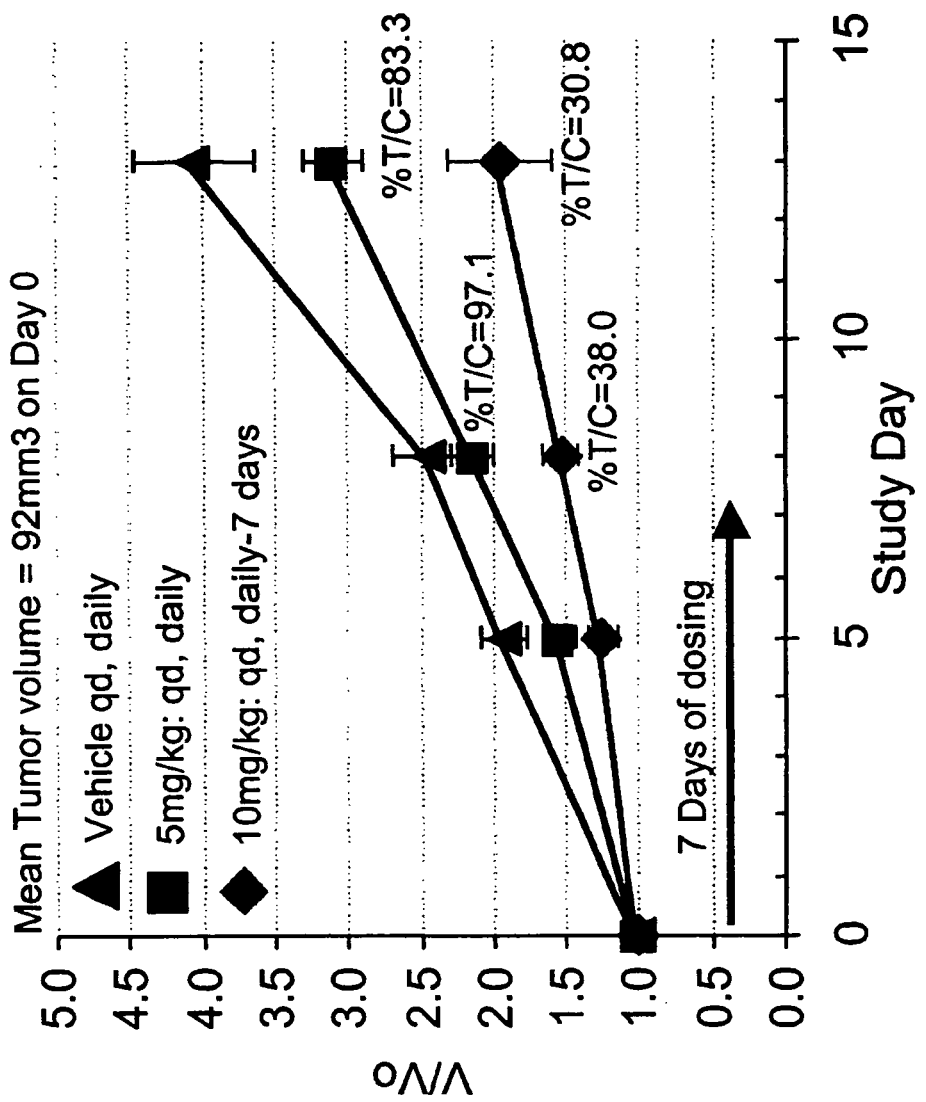

STEREOISOMERICALLY ENRICHED 3-AMINOCARBONYL BICYCLOHEPTENE PYRIMIDINEDIAMINE COMPOUNDS AND THEIR USES

1. CROSS-REFERENCE TO RELATED APPLICATION

This application claims benefit under 35 U.S.C. §119(e) to application Ser. No. 60/628,199 filed Nov. 15, 2004, the contents of which are incorporated herein by reference.

2. FIELD

The present disclosure relates to stereoisomerically enriched compositions of 4N-(3-aminocarbonylbicyclo [2.2.1]hept-5-en-2-yl)-N2-substituted phenyl-2,4-pyrimidinediamine compounds that exhibit antiproliferative activity, prodrugs of the compounds, intermediates and methods of synthesis for making the compounds and/or prodrugs, pharmaceutical compositions comprising the compounds and/or prodrugs and the use of the compounds and/or prodrugs in a variety of contexts, including, for example, the treatment of proliferative disorders, such as tumors and cancers.

3. BACKGROUND

Cancer is a group of varied diseases characterized by uncontrolled growth and spread of abnormal cells. Generally, all types of cancers involve some abnormality in the control of cell growth and division. The pathways regulating cell division and/or cellular communication become altered in cancer cells such that the effects of these regulatory mechanisms in controlling and limiting cell growth fails or is bypassed. Through successive rounds of mutation and natural selection, a group of abnormal cells, generally originating from a single mutant cell, accumulates additional mutations that provide selective growth advantage over other cells, and thus evolves into a cell type that predominates in the cell mass. This process of mutation and natural selection is enhanced by genetic instability displayed by many types of cancer cells, an instability which is gained either from somatic mutations or by inheritance from the germ line. The enhanced mutability of cancerous cells increases the probability of their progression towards formation of malignant cells. As the cancer cells further evolve, some become locally invasive and then mestasize to colonize tissues other than the cancer cell's tissue of origin. This property along with the heterogeneity of the tumor cell population makes cancer a particularly difficult disease to treat and eradicate.

Traditional cancer treatments take advantage of the higher proliferative capacity of cancer cells and their increased sensitivity to DNA damage. Ionizing radiation, including γ-rays and x-rays, and cytotoxic agents, such as bleomycin, cis-platin, vinblastine, cyclophosphamide, 5'-fluorouracil, and methotrexate rely upon a generalized damage to DNA and destabilization of chromosomal structure which eventually lead to destruction of cancer cells. These treatments are particularly effective for those types of cancers that have defects in cell cycle checkpoint, which limits the ability of these cells to repair damaged DNA before undergoing cell division. The non-selective nature of these treatments, however, often results in severe and debilitating side effects. The systemic use of these drugs may result in damage to normally healthy organs and tissues, and compromise the long-term health of the patient.

Although more selective chemotherapeutic treatments have been developed based on knowledge of how cancer cells develop, for example, the anti-estrogen compound tamoxifen, the effectiveness of all chemotherapeutic treatments are subject to development of resistance to the drugs. In particular, the increased expression of cell membrane bound transporters, such as MdrI, produces a multidrug resistance phenotype characterized by increased efflux of drugs from the cell. These types of adaptation by cancer cells severely limit the effectiveness of certain classes of chemotherapeutic agents. Consequently, identification of other chemotherapeutic agents, particularly active stereoisomers and/or stereoisomeric mixtures is critical for establishing therapies effective for attacking the heterogeneous nature of proliferative disease and for overcoming any resistance that may develop over the course of therapy with other compounds. Moreover, use of combinations of chemotherapeutic agents, including different stereoisomers and/or stereoisomeric mixtures of a particular chemotherapeutic agent, which may have differing properties and cellular targets, increases the effectiveness of chemotherapy and limits the generation of drug resistance.

4. SUMMARY

In one aspect, 4N-(3-aminocarbonylbicyclo[2.2.1]hept-5-en-2-yl)-2N-substituted phenyl-2,4-pyrimidinediamine compounds enriched in specified diastereomers are provided that exhibit antiproliferative activity against a variety of different types of tumor cells. In some embodiments, compounds according to structural formula (I) are provided:

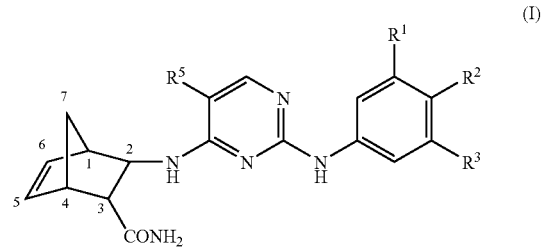

(I)

including prodrugs, salts, hydrates, solvates and N-oxides thereof, that are enriched in the corresponding diastereomer of structural formula (Ia), designated the (1R,2R,3S,4S) diastereomer:

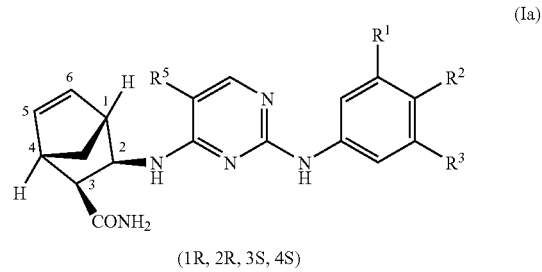

(Ia)

(1R, 2R, 3S, 4S)

wherein:
each $R^1$ is independently selected from the group consisting of hydrogen, lower alkyl, —$(CH_2)_n$—OH, —$OR^a$, —$O(CH_2)_n$—$R^a$, —$O(CH_2)_n$—$R^b$, —$C(O)OR^a$, halo, —$CF_3$ and —$OCF_3$;

each $R^2$ is independently selected from the group consisting of hydrogen, lower alkyl, —$OR^a$, —$O(CH_2)_n$—$R^a$, —$O(CH_2)_n$—$R^b$, —$NHC(O)R^a$, halo, —$CF_3$, —$OCF_3$,

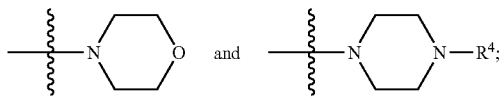

each $R^3$ is independently selected from the group consisting of hydrogen, lower alkyl, —$(CH_2)_n$—OH, —$OR^a$, —$O(CH_2)_n$—$R^a$, —$O(CH_2)_n$—$R^b$, halo, —$CF_3$, —$OCF_3$,

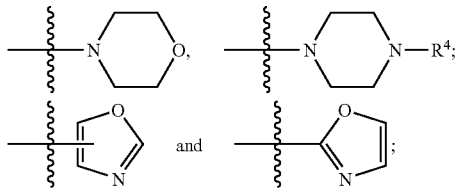

each $R^4$ is independently selected from the group consisting of hydrogen, lower alkyl, arylalkyl, —$OR^a$, —$NR^cR^c$, —$C(O)R^a$, —$C(O)OR^a$ and —$C(O)NR^cR^c$;
$R^5$ is hydrogen, halo, fluoro, —CN, —$NO_2$, —$C(O)OR^a$ or —$CF_3$;
each n is independently an integer from 1 to 3;
each $R^a$ is independently selected from the group consisting of hydrogen, lower alkyl and lower cycloalkyl;
each $R^b$ is independently selected from the group consisting of —$OR^a$, —$CF_3$, —$OCF_3$, —$NR^cR^c$, —$C(O)R^a$, —$C(O)OR^a$, —$C(O)NR^cR^c$ and —$C(O)NR^aR^d$;
each $R^c$ is independently selected from the group consisting of hydrogen and lower alkyl, or, alternatively, two $R^c$ substituents may be taken together with the nitrogen atom to which they are bonded to form a 4-9 membered saturated ring which optionally includes 1-2 additional heteroatomic groups selected from O, $NR^a$, $NR^a$—$C(O)R^a$, $NR^a$—$C(O)OR^a$ and $NR^a$—$C(O)NR^a$; and
each $R^d$ is independently lower mono-hydroxyalkyl or lower di-hydroxyalkyl.

In some embodiments, the compound of structural formula (I) is a racemic mixture of (2-exo-3-exo) cis isomers according to structural formula (IIa):

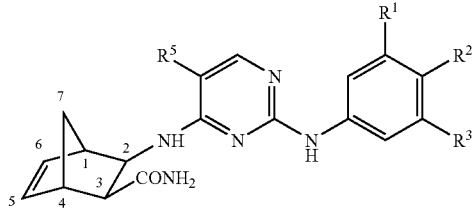

including prodrugs, salts, hydrates, solvates and N-oxides thereof, wherein $R^1$, $R^2$, $R^3$ and $R^5$ are as defined for structural formula (I), supra, In some embodiments, the compound is a stereoisomerically enriched diastereomer according to structural formula (Ia), supra, including prodrugs, salts, hydrates, solvates and N-oxides thereof, that is substantially free of its enantiomer and any other diastereomer thereof.

In still another aspect, prodrugs of the stereoisomerically enriched compounds are provided. Such prodrugs may be active in their prodrug form, or may be inactive until converted under physiological or other conditions of use to an active drug form. In the prodrugs, one or more functional groups of the stereoisomerically enriched compounds are included in promoieties that cleave from the molecule under the conditions of use, typically by way of hydrolysis, enzymatic cleavage or some other cleavage mechanism, to yield the functional groups. For example, primary or secondary amino groups may be included in an amide promoiety that cleaves under conditions of use to generate the primary or secondary amino group. Thus, the prodrugs include special types of protecting groups, termed "progroups," masking one or more functional groups of the compounds that cleave under the conditions of use to yield an active drug compound. Functional groups within the stereoisomerically enriched compounds that may be masked with progroups for inclusion in a promoiety include, but are not limited to, amines (primary and secondary), hydroxyls, sulfanyls(thiols), carboxyls, carbonyls, etc. Myriad progroups suitable for masking such functional groups to yield promoieties that are cleavable under the desired conditions of use are known in the art. All of these progroups, alone or in combination, may be included in the prodrugs. Specific examples of promoieties that yield primary or secondary amine groups that can be included in the prodrugs include, but are not limited to amides, carbamates, imines, ureas, phosphenyls, phosphoryls and sulfenyls. Specific examples of promoieties that yield sulfanyl groups that can be included in the prodrugs include, but are not limited to, thioethers, for example S-methyl derivatives (monothio, dithio, oxythio, aminothio acetals), silyl thioethers, thioesters, thiocarbonates, thiocarbamates, asymmetrical disulfides, etc. Specific examples of promoieties that cleave to yield hydroxyl groups that can be included in the prodrugs include, but are not limited to, sulfonates, esters and carbonates. Specific examples of promoieties that yield carboxyl groups that can be included in the prodrugs include, but are not limited to, esters (including silyl esters, oxamic acid esters and thioesters), amides and hydrazides.

In still another aspect, compositions comprising one or more stereoisomerically enriched compounds are provided. The compositions generally comprise the compound(s), and/or prodrugs, salts, hydrates, solvates and/or N-oxides thereof, and an appropriate carrier, excipient and/or diluent. The exact nature of the carrier, excipient and/or diluent will depend upon the desired use for the composition, and may range from being suitable or acceptable for in vitro uses, to being suitable or acceptable for veterinary uses, to being suitable or acceptable for use in humans.

The stereoisomerically enriched compounds described herein are potent inhibitors of proliferation abnormal cells, such as tumor cells, in in vitro assays. Thus, in still another aspect, methods of inhibiting proliferation of abnormal cells, and in particular tumor cells, are provided. The methods generally involve contacting an abnormal cell, such as a tumor cell, with an amount of one or more stereoisomerically enriched compounds described herein, and/or prodrugs, salts, hydrates, solvates and/or N-oxides thereof, effective to inhibit proliferation of the cell. The cells can be contacted with the compound per se, or the compound can be formulated into a composition. The methods may be practiced in in vitro contexts, or in in vivo contexts as a therapeutic approach towards the treatment or prevention of proliferative disorders, such as tumorigenic cancers.

In still another aspect, methods of treating proliferative disorders are provided. The methods may be practiced in animals in veterinary contexts or in humans. The methods generally involve administering to an animal or human subject an amount of one or more stereoisomerically enriched compounds described herein, and/or prodrugs, salts, hydrates, solvates and/or N-oxides thereof, effective to treat or prevent the proliferative disorder. The compound(s) per se can be administered to the subject, or the compound(s) can be administered in the form of a composition. Proliferative disorders that can be treated according to the methods include, but are not limited to, tumorigenic cancers.

The stereoisomerically enriched compounds described herein are potent inhibitors of Aurora kinases. Aurora kinases are a family of enzymes known to be key regulators of cell division. Elevated levels of Aurora kinases have been found in several types of human cancer cells, such as breast, colon, renal, cervical, neuroblastomer, melanoma, lymphoma, pancreatic, prostate and other solid tumors (see, e.g., Bischott et al., 1998, EMBO J. 17:3052-3065; Geopfert & Brinkley, 2000, Curr. Top. Dev. Biol. 49:331-342; Sakakura et al., 2001, Br. J. Cancer 84:824-831), and overexpression of Aurora kinases has been shown to result in cell transformation, a process by which normal cells become cancers. Although not intending to be bound by any particular theory of operation, it is believed that the stereoisomerically enriched compounds described herein, as well as the active prodrugs, salts, hydrates, solvates and/or N-oxides thereof, exert their antiproliferative activity by inhibiting one or more Aurora kinases.

Thus, in yet another aspect, methods of inhibiting an activity of an Aurora kinase are provided. The methods generally involve contacting an Aurora kinase with an amount of one or more stereoisomerically enriched compounds described herein, and/or active prodrugs, salts, hydrates, solvates and/or N-oxides thereof, effective to inhibit its activity. The methods can be practiced in in vitro contexts with purified or partially purified Aurora kinase enzymes (e.g., with extracts of cells expressing an Aurora kinase), in in vitro contexts with intact cells expressing an Aurora kinase, or in in vivo contexts to inhibit an Aurora kinase-mediated process (for example cellular mitotis) and/or as a therapeutic approach towards the treatment or prevention of diseases or disorders that are mediated, at least in part, by Aurora kinase activity.

In still another aspect, methods of treating or preventing Aurora kinase-mediated diseases or disorders are provided. The methods generally involve administering to an animal or human subject an amount of one or more stereoisomerically enriched compounds described herein, and/or active prodrugs, salts, hydrates, solvates and/or N-oxides thereof, effective to treat or prevent the Aurora kinase-mediated disease or disorder. Aurora kinase-mediated diseases and disorders include any disease, disorder, or other deletarions condition in which a member of the Aurora kinase family of enzymes plays a role. Specific examples of such Aurora kinase-mediated diseases or disorders include, but are not limited to, melanoma, leukemia, and solid tumor cancers, such as, for example, colon, breast, gastric, ovarian, cervical, melanoma, renal, prostate, lymphoma, neuroblastoma, pancreatic and bladder cancers.

Other aspects include, but are not limited to, intermediates and methods useful for synthesizing the stereoisomerically enriched compounds and prodrugs, as will be described in more detail herein below.

5. BRIEF DESCRIPTION OF THE DRAWINGS

FIGS. 1-4 illustrate the inhibitory effect of (1R,2R,3S,4S)-N4-(3-aminocarbonylbicyclo[2.2.1]hept-5-ene-2-yl)-5-fluoro-N2-[3-methyl-4-(4-methylpiperazin-yl)phenyl]-2,4-pyrimidinediamine bis hydrogen chloride salt (compound 60a.2HCl) on the growth of various different types of tumors in standard xenograft treatment and regression models.

6. DETAILED DESCRIPTION

6.1 Definitions

As used herein, the following terms are intended to have the following meanings:

"Alkyl" by itself or as part of another substituent refers to a saturated or unsaturated branched, straight-chain or cyclic monovalent hydrocarbon radical having the stated number of carbon atoms (i.e., C1-C6 means one to six carbon atoms) that is derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl , prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" is used, as defined below. "Lower alkyl" refers to an alkyl group containing from 1 to 6 carbon atoms.

"Alkanyl" by itself or as part of another substituent refers to a saturated branched, straight-chain or cyclic alkyl derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" by itself or as part of another substituent refers to an unsaturated branched, straight-chain or cyclic alkyl having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl ; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1 -en-3-yl, cyclobuta-1,3-dien-1-yl, etc.; and the like.

"Alkynyl" by itself or as part of another substituent refers to an unsaturated branched, straight-chain or cyclic alkyl having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkydidyl" by itself or as part of another substituent refers to a saturated or unsaturated, branched, straight-chain or cyclic divalent hydrocarbon group having the stated number of carbon atoms (i.e., C1-C6 means from one to six carbon atoms) derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the sane or different atoms. Typical alkyldiyl groups include, but are not limited to, methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Where it is specifically intended that the two valencies be on the same carbon atom, the nomenclature "alkylidene" is used. A "lower alkyldiyl" is an alkyldiyl group containing 1 to 6 carbon atoms. In some embodiments the alkyldiyl groups are saturated acyclic alkanyldiyl groups in which the radical centers are at the terminal carbons, e.g., methandiyl (methano); ethan-1,2-diyl(ethano); propan-1,3-diyl(propano); butan-1,4-diyl(butano); and the like (also referred to as alkylenes, defined infra).

"Alkylene" by itself or as part of another substituent refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The locant of a double bond or triple bond, if present, in a particular alkylene is indicated in square brackets. Typical alkylene groups include, but are not limited to, methylene (methano); ethylenes such as ethano, etheno, ethyno; propylenes such as propano, prop[1]eno, propa[1,2]dieno, prop[1]yno, etc.; butylenes such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In some embodiments, the alkylene group is (C1-C6) or (C1-C3) alkylene. In some embodiments, the alkylene group is a straight-chain saturated alkano group, e.g., methano, ethano, propano, butano, and the like.

"Cycloalkyl" by itself or as part of another substituent refers to a cyclic version of an "alkyl" group. Typical cycloalkyl groups include, but are not limited to, cyclopropyl; cyclobutyls such as cyclobutanyl and cyclobutenyl; cyclopentyls such as cyclopentanyl and cyclopentenyl; cyclohexyls such as cyclohexanyl and cyclohexenyl; and the like.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, tetrahydronaphthalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, tetrahydronaphthalene, triphenylene, trinaphthalene, and the like.

"Aryl" by itself or as part of another substituent refers to a monovalent aromatic hydrocarbon group having the stated number of carbon atoms (i.e., C5-C15 means from 5 to 15 carbon atoms) derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like, as well as the various hydro isomers thereof. In some embodiments, the aryl group is (C5-C15) aryl, with (C5-C10) being more typical. Specific examples are phenyl and naphthyl.

"Halogen" or "Halo" by themselves or as part of another substituent, unless otherwise stated, refer to fluoro, chloro, bromo and iodo.

"Haloalkyl" by itself or as part of another substituent refers to an alkyl group in which one or more of the hydrogen atoms are replaced with a halogen. Thus, the term "haloalkyl" is meant to include monohaloalkyls, dihaloalkyls, trihaloalkyls, etc. up to perhaloalkyls. For example, the expression "(C1-C2) haloalkyl" includes fluoromethyl, difluoromethyl, trifluoromethyl, 1-fluoroethyl, 1,1-difluoroethyl, 1,2-difluoroethyl, 1,1,1-trifluoroethyl, perfluoroethyl, etc.

"Hydroxyalkyl" by itself or as part of another substituent refers to an alkyl group in which one or more of the hydrogen atoms are replaced with a hydroxyl substituent. Thus, the term "hydroxyalkyl" is meant to include monohydroxyalkyls, dihydroxyalkyls, trihydroxyalkyls, etc.

The above-defined groups may include prefixes and/or suffixes that are commonly used in the art to create additional well-recognized substituent groups. As examples, "alkyloxy" or "alkoxy" refers to a group of the formula —OR, "alkylamine" refers to a group of the formula —NHR and "dialkylamine" refers to a group of the formula —NRR, where each R is independently an alkyl. As another example, "haloalkoxy" or "haloalkyloxy" refers to a group of the formula —OR', where R' is a haloalkyl.

"Prodrug" refers to a derivative of an active compound (drug) that may require a transformation under the conditions of use, such as within the body, to release the active drug. Prodrugs are frequently, but not necessarily, pharmacologically inactive until converted into the active drug. Prodrugs are typically obtained by masking a functional group in the drug compound believed to be in part required for activity with a progroup (defined below) to form a promoiety which undergoes a transformation, such as cleavage, under the specified conditions of use to release the functional group, and hence the active drug. The cleavage of the promoiety may proceed spontaneously, such as by way of a hydrolysis reaction, or it may be catalyzed or induced by another agent, such as by an enzyme, by light, by acid or base, or by a change of or exposure to a physical or environmental parameter, such as a change of temperature. The agent may be endogenous to the conditions of use, such as an enzyme present in the cells to which the prodrug is administered or the acidic conditions of the stomach, or it may be supplied exogenously.

A wide variety of progroups, as well as the resultant promoieties, suitable for masking functional groups in the active stereoisomerically enriched compounds described herein to yield prodrugs are well-known in the art. For example, a hydroxyl functional group may be masked as a sulfonate, ester or carbonate promoiety, which may be hydrolyzed in vivo to provide the hydroxyl group. An amino functional group may be masked as an amide, carbamate, imine, urea, phosphenyl, phosphoryl or sulfenyl promoiety, which may be hydrolyzed in vivo to provide the amino group. A carboxyl group may be masked as an ester (including silyl esters and thioesters), amide or hydrazide promoiety, which may be hydrolyzed in vivo to provide the carboxyl group. Other specific examples of suitable progroups and their respective promoieties will be apparent to those of skill in the art.

"Progroup" refers to a type of protecting group that, when used to mask a functional group within an active stereoisomerically enriched drug compound to form a promoiety, converts the drug into a prodrug. Progroups are typically attached to the functional group of the drug via bonds that are cleavable under specified conditions of use. Thus, a progroup is that portion of a promoiety that cleaves to release the functional group under the specified conditions of use. As a specific example, an amide promoiety of the formula —NH—C(O)CH$_3$ comprises the progroup —C(O)CH$_3$.

"Proliferative disorder" refers to a disease or disorder characterized by aberrant cell proliferation, for example, where cells divide more than their counterpart normal cells. The aberrant proliferation may be caused by any mechanism of action or combination of mechanisms of action. For example, the cell cycle of one or more cells may be affected such that cell(s) divide more frequently than their counterpart normal cells, or as another example, one or more cells may bypass inhibitory signals, which would normally limit their number of divisions. Proliferative diseases include, but are not limited to, slow or fast growing tumors and cancers.

"Antiproliferative compound" refers to a compound that inhibits the proliferation of a cell as compared to an untreated control cell of a similar type. The inhibition can be brought about by any mechanism or combination of mechanisms, and may operate to inhibit proliferation cytostatically or cytotoxically. As a specific example, inhibition as used herein includes, but is not limited to, arrest of cell division, a reduction in the rate of cell division, proliferation and/or growth and/or induction of cell death, by any mechanism of action, including, for example apoptosis.

"Aurora kinase" refers to a member of the family of serine/threonine protein kinases that are generally referred to as "Aurora" kinases. The Aurora family of serine/threonine protein kinases are essential for cell proliferation (see, e.g., Bischhoff & Plowman, 1999, Trends Cell Biol. 9:454-459; Giet & Prigent, 1999, J. Cell Science 112:3591-3601; Nigg, 2001, Nat. Rev. Mol. Cell Biol. 2:21-32; Adams et al., 2001, Trends Cell Biol. 11:49-54). Presently, there are three known mammalian family members: Aurora-A ("2"), Aurora-B ("1") and Aurora-C ("3") (see, e.g., Giet & Prigent, 1999, J. Cell Sci. 112:3591-3601; Bischoff & Plowman, 1999, Trends Cell Biol. 9:454-459). As used herein, "Aurora kinase" includes not only these three known mammalian family members, but also later-discovered mammalian family members and homologous proteins from other species and organisms (for non-limiting examples of homologous members of the Aurora kinase family from other species and organisms see Schumacher et al., 1998, J. Cell Biol. 143:1635-1646; Kimura et al., 1997, J. Biol. Chem. 272:13766-13771).

"Aurora kinase-mediated process" or "Aurora kinase-mediated disease or disorder" refers to a cellular process, disease or disorder in which an Aurora kinase plays a role. The Aurora kinases are believed to play a key role in protein phosphorylation events that regulate the mitotic phase of the cell cycle. The human Aurora kinases display distinct subcellular locations during mitosis. For example, Aurora-A is upregulated during the M phase of the cell cycle and localizes to the spindle pole during mitosis, suggesting involvement in centrosomal functions. While Aurora-A activity is maximized during prophase, Aurora-B is believed to play an important role during chromatid separation and formation of the cleavage furrow in anaphase and telophase. The role of Aurora-C is less clear, but it has been shown to localize to centrosomes during mitosis from anaphase to cytokinesis. Moreover, inhibition of Aurora kinase activity in mammalian cells leads to abnormal cell growth and polyploidy (Terada et al., 1998, EMBO J. 17:667-676). Thus, Aurora kinases are thought to regulate cell division, chromosome segregation, mitotic spindle formation, and cytokinesis. As used herein, all of these various processes are within the scope of "Aurora kinases-mediated process."

Moreover, since its discovery in 1997, the mammalian Aurora kinase family has been closely linked to tumorigenesis. The most compelling evidence for this is that overexpression of Aurora-A transforms rodent fibroblasts (Bischoff et al., 1998, EMBO J. 17:3052-3065). Cells with elevated levels of this kinase contain multiple centrosomes and multipolar spindles, and rapidly become aneuploid. The oncogenic activity of Aurora kinases is likely to be linked to the generation of such genetic instability. Indeed, a correlation between amplification of the aurora-A locus and chromosomal instability in mammary and gastric tumors has been observed (Miyoshi et al., 2001, Int. J. Cancer 92:370-373; Sakakura et al., 2001, Brit. J. Cancer 84:824-831).

The Aurora kinases have been reported to be over-expressed in a wide range of human tumors. Elevated expression of Aurora-A has been detected in over 50% of colorectal (Bischoff et al., 1998, EMBO J. 17:3052-3065; Takahashi et al., 2000, Jpn. J. Cancer Res. 91:1007-1014), ovarian (Gritsko et al., 2003, Clinical Cancer Research 9:1420-1426, and gastric tumors (Sakakura, 2001, Brit. J. Cancer 84:824-831, and in 94% of invasive duct adenocarcinomas of the breast (Tanaka, 1999, Cancer Research. 59:2041-2044). High levels of Aurora-A have also been reported in renal, cervical, neuroblastoma, melanoma, lymphoma, pancreatic and prostate tumor cell lines (Bischoff et al., 1998, EMBO J. 17:3052-3065; Kimura et al., 1999, J. Biol. Chem. 274:7334-7340; Zhou et al., 1998, Nature Genetics 20:189-193; Li et al., 2003, Clin Cancer Res. 9(3):991-7). Amplification/overexpression of Aurora-A is observed in human bladder cancers and amplification of Aurora-A is associated with aneuploidy and aggressive clinical behavior (Sen et al, 2002, J Natl Cancer Inst. 94(17):1320-9. Moreover, amplification of the aurora-A locus (20q13) correlates with poor prognosis for patients with node-negative breast cancer (Isola et al., 1995, American Journal of Pathology 147:905-911). Aurora-B is highly expressed in multiple human tumor cell lines, including leukemic cells (Katayama et al., 1998, Gene 244:1-7). Levels of this enzyme increase as a function of Duke's stage in primary colorectal cancers (Katayama et al., 1999, J. Nat'l Cancer Inst. 91:1160-1162). Aurora-C, which is normally only found in germ cells, is also over-expressed in a high percentage of primary colorectal cancers and in a variety of tumor cell lines including cervical adenocarcinoma and breast carcinoma cells (Kimura et al., 1999, J. Biol. Chem. 274:7334-7340; Takahashi et al., 2000, Jpn. J. Cancer Res. 91:1007-1014).

In contrast, the Aurora family is expressed at a low level in the majority of normal tissues, the exceptions being tissues with a high proportion of dividing cells, such as the thymus and testis (Bischoff et al., 1998, EMBO J., 17:3052-3065).

For a further review of the role(s) Aurora kinases play in proliferative disorders, see Bischhoff & Plowman, 1999, Trends Cell Biol. 9:454-459; Giet & Prigent, 1999, J. Cell Science 112:3591-3601; Nigg, 2001, Nat. Rev. Mol. Cell Biol. 2:21-32; Adams et al., 2001, Trends Cell Biol. 11:49-54 and Dutertre et al., 2002, Oncogene 21:6175-6183.

Although over-expression of proteins by cancer cells is not always indicative that inhibition of the protein activity will yield anti-tumor effect, it has been confirmed in functional assays that at least the following types of tumor cells are sensitive to inhibition of Aurora kinase activity: prostate (DU145), cervical (Hela), pancreatic (Mia-Paca2, BX-PC3), histological leukemia (U937), lung adenocarinoma, lung epidermoid, small lung cell carcinoma, breast, renal carcinoma, MolT3 (all) and Molt4 (all).

Based on the established role of Aurora kinases in a variety of cancers, examples of "Aurora kinases-mediated diseases and disorders" include, but are not limited to, melanoma, leukemia, and solid tumor cancers, such as, for example, colon, breast, gastric, ovarian, cervical, melanoma, renal, prostate, lymphoma, neuroblastoma, pancreatic and bladder cancers.

"Therapeutically effective amount" refers to an amount of a compound sufficient to treat a specified disorder, or disease or one or more of its symptoms. In reference to tumorigenic proliferative disorders, a therapeutically effective amount comprises an amount sufficient to, among other things, cause the tumor to shrink, or to decrease the growth rate of the tumor.

In many situations, standard treatments for tumorigenic proliferative disorder involves surgical interaction to remove the tumor(s), either alone or in combination with drug (chemo) and/or radiation therapies. As used herein, a "therapeutically effect amount" of a compound is intended to include an amount of compound that either prevents the recurrance of tumors in subjects that have had tumor(s) surgically removed, or slows the rate of recurrance of tumor(s) in such subjects.

Accordingly, as used herein, amounts of compounds that provide therapeutic benefit adjunctive to another type of therapy, such as surgical intervention and/or treatment with other antiproliferative agents, including, for example, 5-fluorouracil, vinorelbine, taxol, vinblastine, cisplatin, topotecan, etc.), are included within the meaning of "therapeutically effective amount."

"Prophylactically effective amount" refers to an amount of a compound sufficient to prevent a subject from developing a specified disorder or disease. Typically, subjects in which prophylaxis is practiced are not suffering from the specified disorder or disease, but are recognized as being at an elevated risk for developing this disease or disorder based factors such as, but not limited to, diagnostic markers and family history.

6.2 Stereoisomerically Enriched and Stereoisomerically Pure Compounds

It has been recently discovered that certain N4-(3-aminocarbonylbicyclo[2.2.1]hept-5-ene-2-y1)-N2-substituted phenyl-2,4-pyrimidinediamine compounds, represented by structural formula (I), below, are potent inhibitors of Aurora kinase activity and tumor cell proliferation in in vitro assays (see, e.g., application Ser. No. 11/133,419 filed May 18, 2005, co-pending application Ser. No. 11/281,186, entitled "Stereoisomerically Enriched β-Lactams Using Candida Antarctica," filed concurrently herewith, and international application No. PCT/US05/17470 filed May 18, 2005 and the priority applications referenced therein):

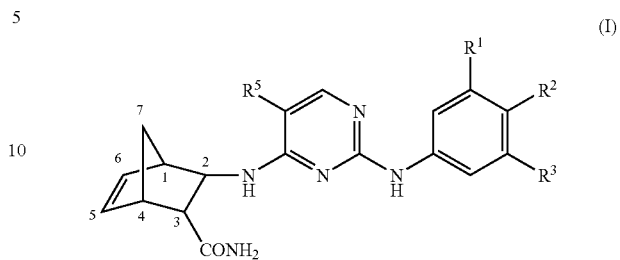

Skilled artisans will appreciate that in structural formula (I), the stereochemistry at carbons 1, 2, 3 and 4 is unspecified, such that the compounds according to structural formula (I) include eight diastereomers, illustrated by structural formulae (Ia)-(Ih), below:

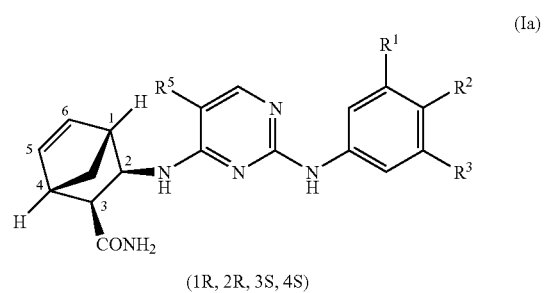

(1R, 2R, 3S, 4S)

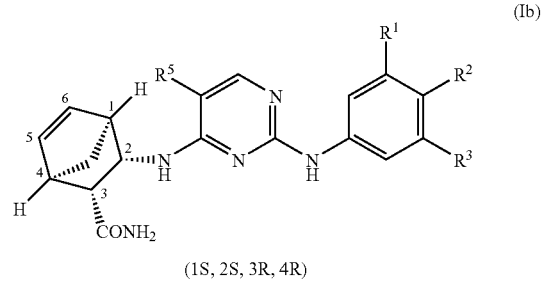

(1S, 2S, 3R, 4R)

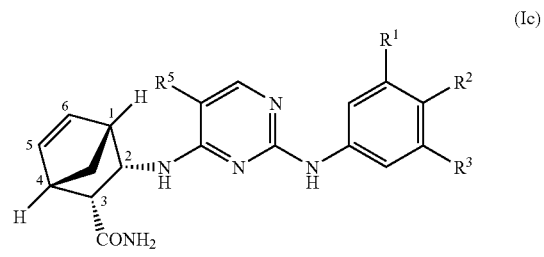

(1R, 2S, 3R, 4S)

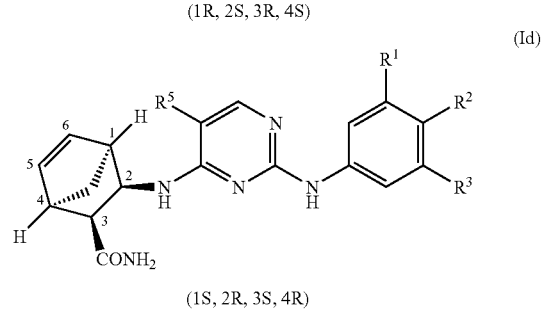

(1S, 2R, 3S, 4R)

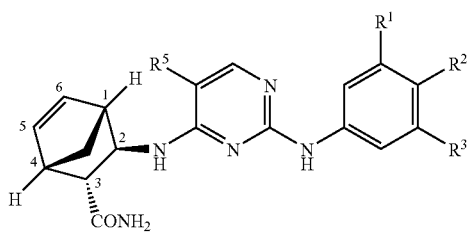

(1R, 2R, 3R, 4S) (Ie)

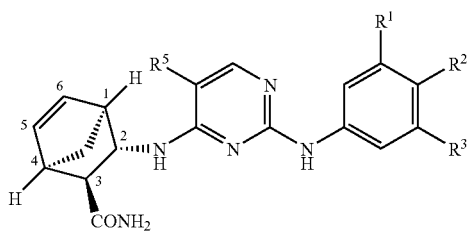

(1S, 2S, 3S, 4R) (If)

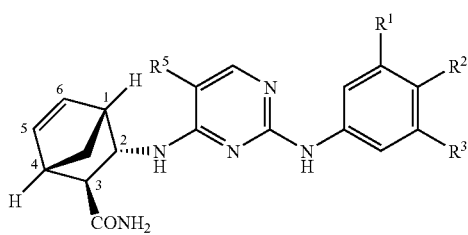

(1R, 2S, 3S, 4S) (Ig)

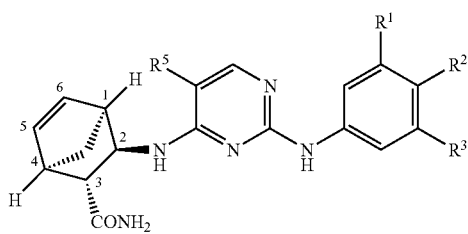

(1S, 2R, 3R, 4R) (Ih)

The compounds of structural formula (I) also include two cis racemates, represented by structural formulae (IIa) and (IIb), and two trans racemates, represented by structural formulae (IIIa) and (IIIb), below:

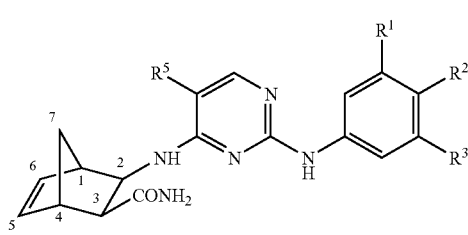

(2-exo-3-exo) (IIa)

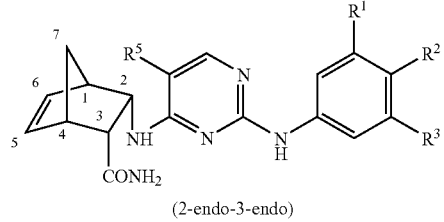

(2-endo-3-endo) (IIb)

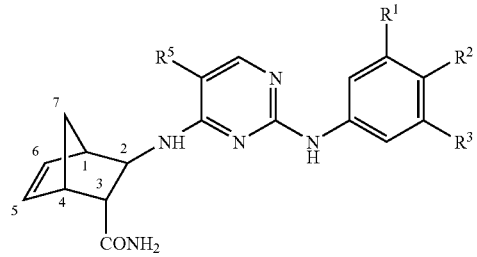

(2-exo-3-endo) (IIIa)

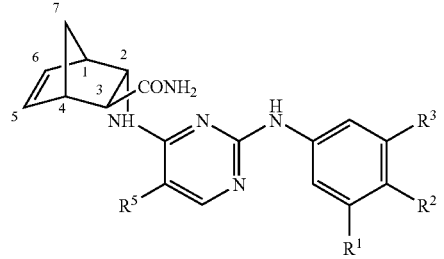

(2-endo-3-exo) (IIIb)

The cis racemate of structural formula (IIa) can be referred to as the 2-exo-3-exo racemate, and includes the (1R,2R,3S, 4S) and (1S,2S,3R,4R) diastereomers of structural formulae (Ia) and (Ib), respectively. The cis racemate of structural formula (IIb) can be referred to as the 2-endo-3-endo racemate, and includes the (1R, 2S, 3R, 4S) and (1S, 2R, 3S, 4R) diastereomers structural formulae (Ic) and (Id), respectively. As described in more detail in the Examples section, for compounds in which $R^5$ is fluoro, $R^1$ is hydrogen, $R^2$ is 4-methylpiperazin-1-yl and $R^3$ is methyl, these two cis racemates exhibit antiproliferative activity against a variety of different tumor cell lines in in vitro antiproliferation assays. However, this 2-exo-3-exo racemate (racemate r1) is approximately twenty-fold more potent than the corresponding 2-endo-3-endo racemate (racemate r2) in all cell lines tested with both racemates. Moreover, it has been discovered that the (1R,2R, 3S,4S) diastereomer of racemate r1 is largely responsible for the potency of the racemate r1. When tested as isolated stereoisomers, this (1R,2R,3S,4S) diastereomer (designated the "a" diastereomer) generally exhibited IC50's in the nanomolar range, whereas the (1S,2S,3R,4R) diastereomer (designated the "b" enantiomer) generally exhibited IC50's in the micromolar range against the same cell lines. Thus, in general, the (1R,2R,3S,4S) diastereomer of this compound is generally 1000-fold more potent than its corresponding (1S, 2S,3R,4R) enantiomer. It is also approximately 20-50 times more potent than the corresponding 2-endo-3-endo r2 racemate in the cell lines tested. The (1R,2R,3S,4S) diastereomer exhibited similarly superior results compared to its (1S,2S, 3R,4R) enantiomer in cell-based inhibition assays against Aurora kinase B. Based on the observed potency of this (1R,2R,3S,4S) diastereomer, it is expected that the full range of (1R,2R,3S,4S) diastereomers according to structural formula (Ia) will exhibit similarly superior potencies as compared to their corresponding (1S,2S,3R,4R) enantiomers, 2-exo-3-exo racemates, 2-endo-3-endo racemates and other corresponding diastereomers.

Accordingly, provided herein are compounds that are enriched in this particularly potent (1R,2R,3S,4S) diastereomer. In one embodiment, such stereoisomerically enriched compounds include compounds according to structural formula (I):

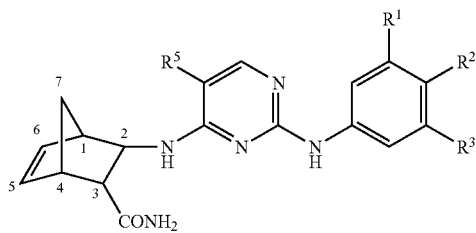

that are enriched in the corresponding diastereomer of structural formula (Ia):

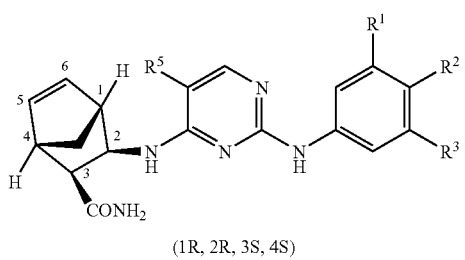

(1R, 2R, 3S, 4S)

wherein:

each R¹ is independently selected from the group consisting of hydrogen, lower alkyl, —(CH₂)ₙ—OH, —ORᵃ, —O(CH₂)ₙ—Rᵃ, —O(CH₂)ₙ—Rᵇ, —C(O)ORᵃ, halo, —CF₃ and —OCF₃;

each R² is independently selected from the group consisting of hydrogen, lower alkyl, —ORᵃ, —O(CH₂)ₙ—Rᵃ, —O(CH₂)ₙ—Rᵇ, —NHC(O)Rᵃ, halo, —CF₃, —OCF₃,

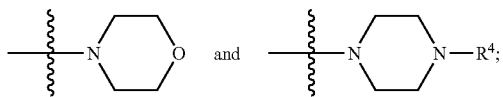

each R³ is independently selected from the group consisting of hydrogen, lower alkyl, —(CH₂)ₙ—OH, —ORᵃ, —O(CH₂)ₙ—Rᵃ, —O(CH₂)ₙ—Rᵇ, halo, —CF₃, —OCF₃,

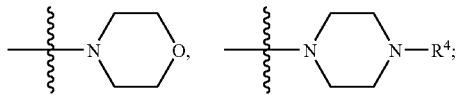

-continued

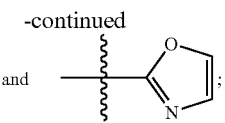

each R⁴ is independently selected from the group consisting of hydrogen, lower alkyl, arylalkyl, —ORᵃ, —NRᶜRᶜ, —C(O)Rᵃ, —C(O)ORᵃ and —C(O)NRᶜRᶜ;

R⁵ is hydrogen, halo, fluoro, —CN, —NO₂, —C(O)ORᵃ, or —CF₃;

each n is independently an integer from 1 to 3;

each Rᵃ is independently selected from the group consisting of hydrogen, lower alkyl and lower cycloalkyl;

each Rᵇ is independently selected from the group consisting of —OR, —CF₃, —OCF₃, —NRᶜRᶜ, —C(O)Rᵃ, —C(O)ORᵃ, —C(O)NRᶜRᶜ and —C(O)NRᵃRᵈ;

each Rᶜ is independently selected from the group consisting of hydrogen and lower alkyl, or, alternatively, two Rᶜ substituents may be taken together with the nitrogen atom to which they are bonded to form a 4-9 membered saturated ring which optionally includes 1-2 additional heteroatomic groups selected from O, NRᵃ, NRᵃ—C(O)Rᵃ, NRᵃ—C(O)ORᵃ and NRᵃ—C(O)NRᵃ; and each Rᵈ is independently lower mono-hydroxyalkyl or lower di-hydroxyalkyl.

In another embodiment, such stereoisomerically enriched compounds include 2-exo-3-exo cis racemates according to structural formula (IIa), wherein R¹, R², R³, R⁴ and R⁵ are as previously defined for structural formula (I), that are enriched in the diastereomer of structural formula (Ia), supra.

As used herein, a compound is "enriched" in a particular diastereomer when that diastereomer is present in excess over any other diastereomer present in the compound. The actual percentage of the particular diastereomer comprising the compound will depend upon the number of other diastereomers present. As a specific example, a racemic mixture is "enriched" in a specified enantiomer when that enantiomer constitutes greater than 50% of the mixture. Regardless of the number of diastereomers present, a compound that is enriched in a particular diastereomer will typically comprise at least about 60%, 70%, 80%, 90%, or even more, of the specified diastereomer. The amount of enrichment of a particular diastereomer can be confirmed using conventional analytical methods routinely used by those of skill in the art, as will be discussed in more detail, below.

In another embodiment, the stereoisomerically enriched compounds include compounds according to structural formula (Ia), supra, wherein R¹, R², R³, R⁴ and R⁵ are as previously defined for structural formula (I), that are substantially free of the corresponding enantiomer and/or any other corresponding diastereomer. By "substantially free of" is meant that the compound comprises less than about 10% of the undesired diastereomers and/or enantiomers as established using conventional analytical methods routinely used by those of skill in the art (discussed in more detail below). In some embodiments, the amount of undesired stereoisomers may be less than 10%, for example, 9%, 8%, 7%, 6%, 5%, 4%, 3%, 2%, 1% or even less. Stereoisomerically enriched compounds that contain about 95% or more of the desired stereoisomer are referred to herein as "substantially pure" stereoisomers. Stereoisomerically enriched compounds that contain about 99% or more of the desired stereoisomer are referred to herein as "pure" stereoisomers. The purity of any stereoisomerically enriched compound (diastereoisomeric purity; % de) can be confirmed using conventional analytical methods, as will be described in more detaile, below.

In some embodiments of the various stereoisomerically enriched compounds described herein, $R^1$ is hydrogen; $R^2$ is

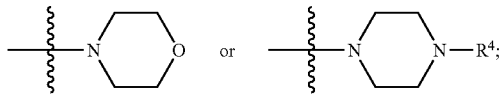

and $R^3$ is other than

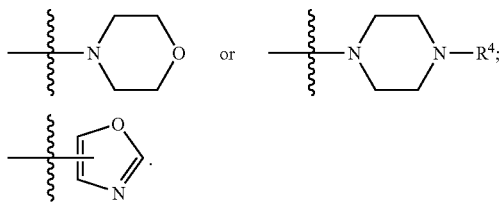

In other embodiments of the various stereoisomerically enriched compounds described herein, $R^3$ is hydrogen, methyl, methoxy, trifluoromethyl or cholor. In still other embodiments, $R^4$ is methyl, —C(O)CH$_3$, —C(O)OCH$_3$ or —C(O)OCH$_2$CH$_3$.

In still other embodiments of the various stereoisomerically enriched compounds described herein, $R^1$ is hydrogen, $R^2$ is other than

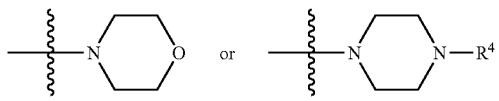

and $R^3$ is

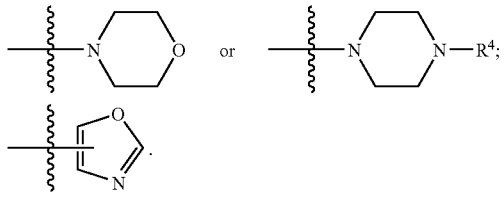

In yet other embodiments, $R^2$ is hydrogen, methyl, methoxy, trifluoromethyl or chloro. Perferably, $R^4$ is methyl, —C(O)CH$_3$, —C(O)OCH$_3$ or —C(O)CH$_2$CH$_3$.

In still other embodiments of the various stereoisomerically enriched compounds described herein, $R^2$ is other than

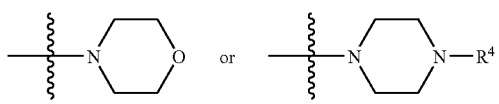

and $R^3$ is other than

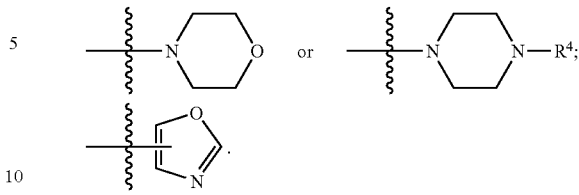

In still other embodiments, $R^1$ and $R^2$ are each hydrogen and $R^3$ is —OCH$_2$NHR$^a$. In some other embodiments, $R^1$, $R^2$ and $R^3$ are each, independently of one another selected from the group consisting of hydrogen, methyl, methoxy, trifluouromethyl and chloro, with the proviso that at least two of $R^1$, $R^2$ and $R^3$ are other than hydrogen.

In still other embodiments, $R^1$ is hydrogen, $R^2$ is selected from the group consisting of hydrogen,

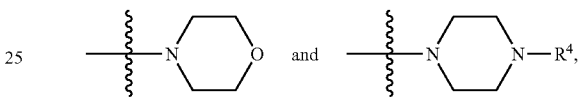

and $R^3$ is selected from the group consisting of hydrogen, lower alkyl, halo, —CF$_3$,

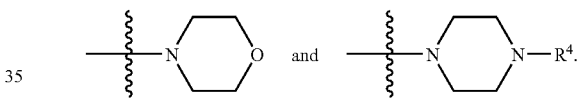

In still other embodiments, $R^3$ is selected from the group consisting of hydrogen, methyl, chloro, —CF$_3$,

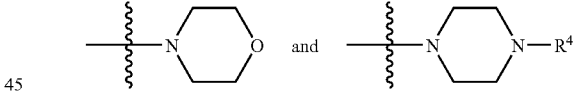

and $R^4$ is methyl, —COR$^a$ or —CO(O)R$^a$ where R$^a$ is methyl or ethyl. In yet another embodiment, $R^2$ is selected from the group consisting of hydrogen,

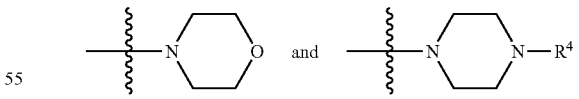

and $R^3$ is selected from the group consisting of hydrogen, lower alkyl, halo, —CF$_3$,

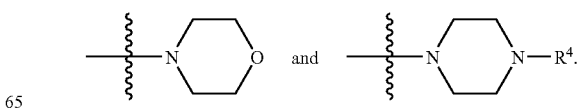

In still other embodiments, $R^3$ is selected from the group consisting of hydrogen, methyl, chloro, —$CF_3$,

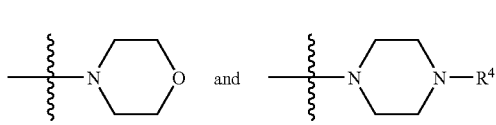

and $R^4$ is methyl, —$COR^a$ or —$CO(O)R^a$ wherein $R^a$ is methyl or ethyl. Preferably, $R^2$ is

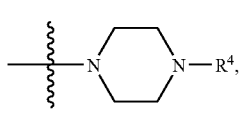

$R^4$ is —$COR^a$ wherein $R^a$ is methyl; and $R^3$ is hydrogen. In other embodiments, $R^2$ is

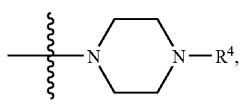

$R^4$ is —$CO(O)R^a$ wherein $R^a$ is ethyl, and $R^3$ is hydrogen. In still another embodiment, $R^2$ is

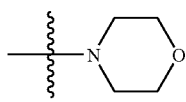

and $R^3$ is hydrogen.

In yet another embodiment, $R^2$ is hydrogen; $R^3$ is

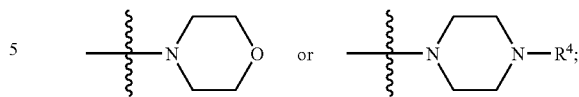

and $R^4$ is methyl, —$COR^a$ or —$CO(O)R^a$ where $R^a$ is methyl or ethyl. Preferably, $R^2$ is

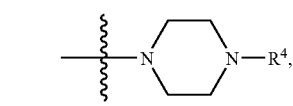

$R^4$ is methyl and $R^3$ is selected from the group consisting of hydrogen, methyl, chloro and —$CF_3$. More preferably, $R^3$ is methyl.

In still other embodiments of the stereoisomerically enriched compounds described herein, $R^5$ is fluoro.

In still other embodiments, the stereoisomerically enriched compound is substantially stereoisomerically pure or stereoisomerically pure (1R,2R,3S,4S)-N4-(3-aminocarbonylbicyclo[2.2.1]hept-5-ene-2-yl)-5-fluoro-N2-[3-methyl-4-(4-methylpiperazin-1-yl)phenyl]-2,4-pyrimidinediamine.

Additional exemplary embodiments of compounds according to structural formula (I) that may be stereoisomerically enriched in the corresponding diastereomer of structural formula (Ia), supra, substantially free of any enantiomers and/or diastereomer thereof, and/or substantially pure or pure in the diastereomer of structural formula (Ia), supra, are illustrated in TABLE 1, below:

TABLE 1

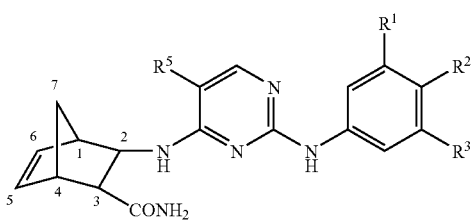

| Compound | $R^1$ | $R^2$ | $R^3$ | $R^5$ |
|---|---|---|---|---|
| 60 | H | 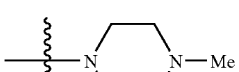 | Me | F |
| 62 | H | 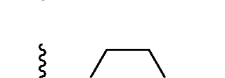 | H | F |
| 64 | H | H | 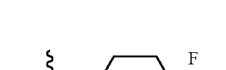 | |

TABLE 1-continued (I)

| Compound | R¹ | R² | R³ | R⁵ |
|---|---|---|---|---|
| 66 | H | piperazine-N-C(O)Me | H | F |
| 68 | H | H | piperazine-N-C(O)Me | F |
| 70 | H | morpholine | H | F |
| 72 | H | piperazine-N-C(O)OEt | H | F |
| 74 | H | H | morpholine | F |
| 76 | H | H | piperazine-N-C(O)OEt | F |
| 78 | H | N-methylpiperazine | Cl | F |
| 80 | H | N-methylpiperazine | H | F |
| 82 | H | N-methylpiperazine | Me | F |
| 84 | H | N-methylpiperazine | CF₃ | F |
| 86 | H | N-methylpiperazine | Cl | F |
| 88 | H | N-methylpiperazine | CF₃ | F |

TABLE 1-continued

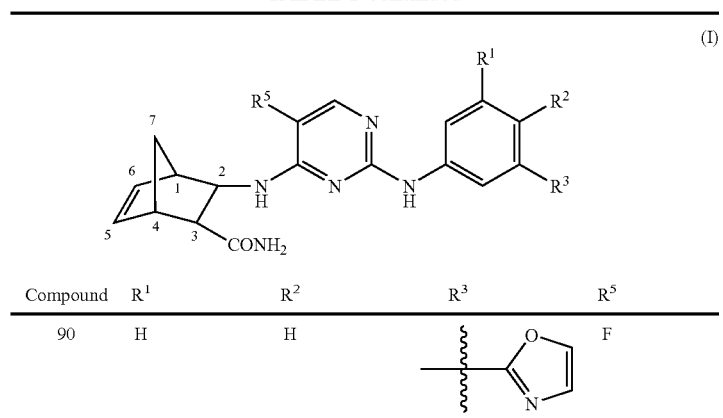

| Compound | R¹ | R² | R³ | R⁵ |
|---|---|---|---|---|
| 90 | H | H | ![oxazole group] | F |

When specific diastereomers and/or racemic mixtures of specific compounds described herein, such as the compounds described in TABLE 1, are intended, the compound number is followed by a letter specifying the specific diastereomer or racemic mixture as follows:

a=(1R,2R,3S,4S)
b=(1S,2S,3R,4R)
c=(1R,2S,3R,4S)
d=(1S,2R,3S,4R)
e=(1R,2R,3R,4S)
f=(1S,2S,3S,4R)
g=(1R,2S,3S,4S)
h=(1S,2R,3R,4R)
r1=2-exo-3-exo cis racemate
r2=2-endo-3-endo cis racemate
r3=2-exo-3-endo trans racemate
r4=2-endo-3-exo trans racemate Thus, as a specific example, the (1R,2R,3S,4S) diastereomer of compound 60 is referred to as compound 60a.

Those of skill in the art will appreciate that the stereoisomerically enriched compounds described herein may include functional groups that can be masked with progroups to create prodrugs. Such prodrugs are usually, but need not be, pharmacologically inactive until converted into their active drug form. For example, ester groups commonly undergo acid-catalyzed hydrolysis to yield the parent carboxylic acid when exposed to the acidic conditions of the stomach, or base-catalyzed hydrolysis when exposed to the basic conditions of the intestine or blood. Thus, when administered to a subject orally, stereoisomerically enriched compounds that include ester moieties may be considered prodrugs of their corresponding carboxylic acid, regardless of whether the ester form is pharmacologically active.

Included within the scope of the invention are prodrugs of the various stereoisomerically enriched compounds described herein. In such prodrugs, any available functional moiety may be masked with a progroup to yield a prodrug. Functional groups within the stereochemically enriched compounds described herein that may be masked with progroups for inclusion in a promoiety include, but are not limited to, amines (primary and secondary), hydroxyls, sulfanyls (thiols), carboxyls, etc. Myriad progroups suitable for masking such functional groups to yield promoieties that are cleavable under the desired conditions of use are known in the art. All of these progroups, alone or in combinations, may be included in the stereoisomerically enriched prodrugs of the invention.

In one illustrative embodiment, the stereoisomerically enriched prodrugs are compounds according to structural formulae (I), supra, in which $R^a$, $R^b$ and $R^c$ may be, in addition to their previously-defined alternatives, a progroup, that are enriched in the corresponding diastereomer of structural formula (Ia), supra.

Those of skill in the art will appreciate that many of the compounds and prodrugs described herein, as well as the various compound species specifically described and/or illustrated herein, may exhibit the phenomena of tautomerism and conformational isomerism. For example, the compounds and prodrugs may exist in several tautomeric forms, including the enol form, the keto form and mixtures thereof. As the various compound names, formulae and compound drawings within the specification and claims can represent only one of the possible tautomeric or conformational forms, it should be understood that the invention encompasses any tautomers or conformational isomers, of the compounds or prodrugs having one or more of the utilities described herein, as well as mixtures of these various different isomeric forms. In cases of limited rotation around the 2,4-pyrimidinediamine core structure, atropisomers are also possible and are also specifically included in the compounds and/or prodrugs of the invention.

Depending upon the nature of the various substituents, the stereoisomerically enriched compounds and prodrugs may be in the form of salts. Such salts include salts suitable for pharmaceutical uses ("pharmaceutically-acceptable salts"), salts suitable for veterinary uses, etc. Such salts may be derived from acids or bases, as is well-known in the art.

In some embodiments, the salt is a pharmaceutically acceptable salt. Generally, pharmaceutically acceptable salts are those salts that retain substantially one or more of the desired pharmacological activities of the parent compound and which are suitable for administration to humans. Pharmaceutically acceptable salts include acid addition salts formed with inorganic acids or organic acids. Inorganic acids suitable for forming pharmaceutically acceptable acid addition salts include, by way of example and not limitation, hydrohalide acids (e.g., hydrochloric acid, hydrobromic acid, hydriodic, etc.), sulfuric acid, nitric acid, phosphoric acid, and the like. Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl)benzoic acid, cinnamic acid, mandelic acid, alkylsulfonic acids (e.g., methanesulfonic acid, ethanesulfonic acid, 1,2-ethane-disulfonic acid, 2-hydroxyethanesulfonic acid, etc.), arylsulfonic acids (e.g., benzenesulfonic acid, 4-chlorobenzenesulfonic acid, 2-naphthalenesulfonic acid, 4-toluenesulfonic acid, camphorsulfonic acid, etc.), 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

Pharmaceutically acceptable salts also include salts formed when an acidic proton present in the parent compound is either replaced by a metal ion (e.g., an alkali metal ion, an alkaline earth metal ion or an aluminum ion) or coordinates with an organic base (e.g., ethanolamine, diethanolamine, triethanolamine, N-methylglucamine, morpholine, piperidine, dimethylamine, diethylamine, etc.).

The stereoisomerically enriched compounds and prodrugs, as well as the salts thereof, may also be in the form of hydrates, solvates and/or N-oxides, as are well-known in the art.

Stereoisomeric enrichment and/or purity of compounds and prodrug described herein may be established by conventional analytical methods well known to those of skill in the art. For example, use of chiral NMR shift reagents, gas chromatographic analysis using chiral columns, high pressure liquid chromatographic analysis using chiral columns, formation of diastereomeric derivatives through reaction with chiral reagents and conventional analysis may be used to establish the stereoisomeric enrichment and/or purity of a specific stereoisomer. Alternatively, synthesis using starting materials of known stereoisomeric enrichment and/or purity may be used to establish the stereoisomeric enrichment and/or purity of the compounds described herein. Other analytical methods for demonstrating stereoisomeric homogeneity are well within the ambit of the skilled artisan.

6.3 Methods of Synthesis

The stereoisomerically enriched compounds and prodrugs may be synthesized via a variety of different synthetic routes using commercially available starting materials and/or starting materials prepared by conventional synthetic methods. A variety of exemplary synthetic routes that can be used to synthesize the stereoisomerically enriched compounds and prodrugs are described in WO 03/063794 and US 2004/0029902, the disclosures of which are incorporated herein by reference.

For purposes of illustration, an exemplary synthetic scheme that can be used to synthesize the full range of compounds described herein is illustrated in Scheme (I), below:

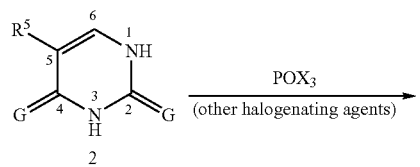

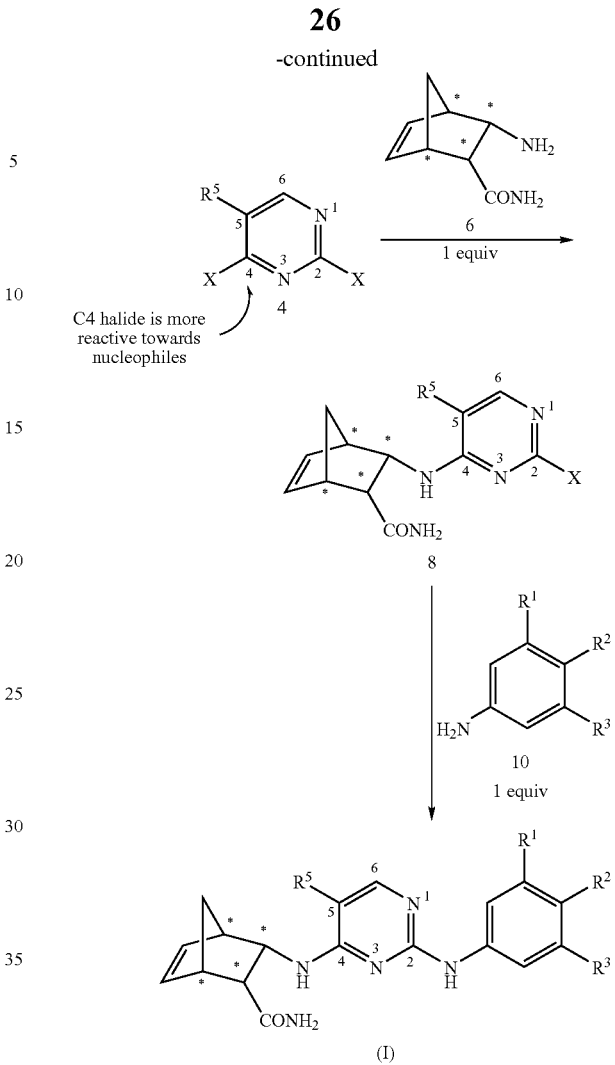

In Scheme (I), $R^1$, $R^2$, $R^3$ and $R^5$ are as previously defined for structural formula (I), supra, X is a halogen (e.g., F, Cl, Br or I), and each G is, independently of the other, selected from O and S. It should be noted that an "*" in aminocarboxamide 6 indicates that the particular stereocenter is not specified. Accordingly, those of skill in the art will appreciate that Scheme (I) may be used to prepare racemic diastereomeric mixtures, diastereomerically enriched mixtures of compounds according to structural formula (I), as well as stereoisomers of the compounds of structural formula (I) that are substantially free of other specified diastereomers.

Referring to Scheme (I), uracil or thiouracil 2 is dihalogenated at the 2- and 4-positions using the standard halogenating agent $POX_3$ (or other halogenating agents) under standard conditions to yield 2,4-bis-halo pyrimidine 4. The halide at the C4 position is more reactive towards nucleophiles than the halide at the C2 position in pyrimidine 4. This differential reactivity can be exploited to synthesize the compounds and prodrugs described herein by first reacting 2,4-bis-halopyrimidine 4 with one equivalent of 2-aminobicyclo[2.2.1]hept-5-ene-3-carboxamide 6, yielding 8, followed by reaction with aniline 10 to yield compounds according to structural formula (I). Those of skill in the art will appreciate that the stereoisomeric configuration and optical purity of aminocarboxamide 6 will, in most circumstances, determine the stereoisomeric configuration and optical purity of the compounds of structural formula (I).

In most situations, the C4 halide is more reactive towards nucleophiles, as illustrated in the Scheme. However, as will be recognized by skilled artisans, the identity of the $R^5$ substituent may alter this reactivity. For example, when $R^5$ is trifluoromethyl, a 50:50 mixture of 4N-substituted-4-pyrimidineamine 8 and the corresponding 2N-substituted-2-pyrimidineamine is obtained. Regardless of the identity of the $R^5$ substituent, the regioselectivity of the reaction can be controlled by adjusting the solvent and other synthetic conditions (such as temperature), as is well-known in the art.

The reactions depicted in Scheme (I) may proceed more quickly when the reaction mixtures are heated via microwave. When heating in this fashion, the following conditions may be used: heat to 175° C. in ethanol for 5-20 min. in a Smith Reactor (Personal Chemistry, Biotage AB, Sweden) in a sealed tube (at 20 bar pressure).

The uracil or thiouracil 2 starting materials may be purchased from commercial sources or prepared using standard techniques of organic chemistry. Commercially available uracils and thiouracils that can be used as starting materials in Scheme (I) include, by way of example and not limitation, uracil (Aldrich #13,078-8; CAS Registry 66-22-8); 2-thiouracil (Aldrich #11,558-4; CAS Registry 141-90-2); 2,4-dithiouracil (Aldrich #15,846-1; CAS Registry 2001-93-6); 5-bromouracil (Aldrich #85,247-3; CAS Registry 51-20-7; 5-fluorouracil (Aldrich #85,847-1; CAS Registry 51-21-8); 5-iodouracil (Aldrich #85,785-8; CAS Registry 696-07-1); 5-nitrouracil (Aldrich #85,276-7; CAS Registry 611-08-5); 5-(trifluoromethyl)-uracil (Aldrich #22,327-1; CAS Registry 54-20-6). Additional 5-substituted uracils and/or thiouracils are available from General Intermediates of Canada, Inc., Edmonton, Calif. (http://www.generalintermediates.com) and/or Interchim, Cedex, France (http://www.interchim.com), or may be prepared using standard techniques. Myriad textbook references teaching suitable synthetic methods are provided infra.

Anilines 10 may be purchased from commercial sources or, alternatively, may be synthesized utilizing standard techniques. For example, suitable anilines may be synthesized from nitro precursors using standard chemistry. Specific exemplary reactions are provided in the Examples section. See also Vogel, 1989, *Practical Organic Chemistry*, Addison Wesley Longman, Ltd. and John Wiley & Sons, Inc.

Skilled artisans will recognize that in some instances anilines 10 may include functional groups that require protection during synthesis. The exact identity of any protecting group(s) used will depend upon the identity of the functional group being protected, and will be apparent to these of skill in the art. Guidance for selecting appropriate protecting groups, as well as synthetic strategies for their attachment and removal, may be found, for example, in Greene & Wuts, *Protective Groups in Organic Synthesis*, 3d Edition, John Wiley & Sons, Inc., New York (1999) and the references cited therein (hereinafter "Greene & Wuts").

Prodrugs as described herein may be prepared by routine modification of the above-described methods.

As skilled artisans will appreciate, the desired (1R,2R,3S, 4S) diastereomer corresponding to structural formula (Ia), supra, can be isolated by chiral separation or other standard techniques. Methods for chirally resolving specific diastereomers are described in more detail in the Examples section.

Stereoisomerically enriched compounds and/or substantially pure and/or pure diastereomers can also be synthesized from 2-amino-3-carboxamide starting materials 6 having specified stereochemistry, or with the aid of chiral auxiliaries.

In one exemplary embodiment, illustrated in Scheme (II), below, the desired diastereomer is resolved chemically using (R)-methyl-p-methoxybenzylamine 18 as a chiral auxiliary.

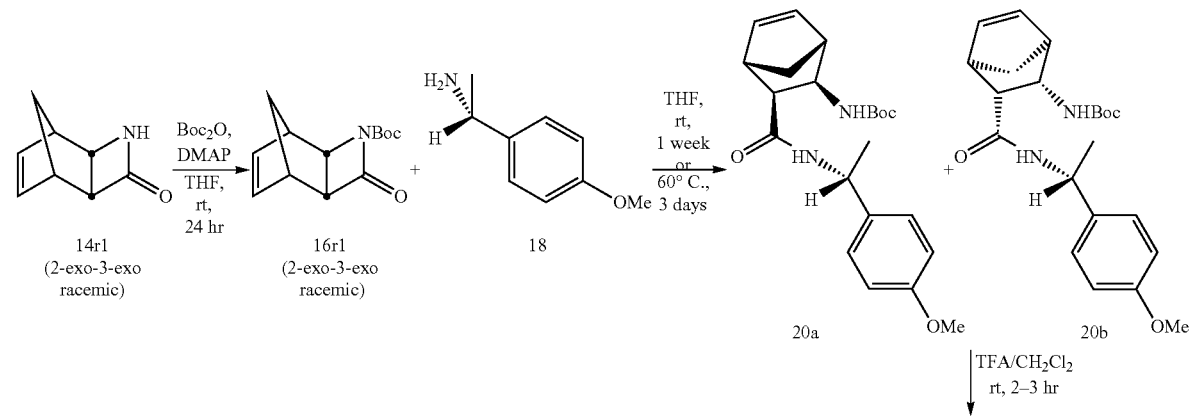

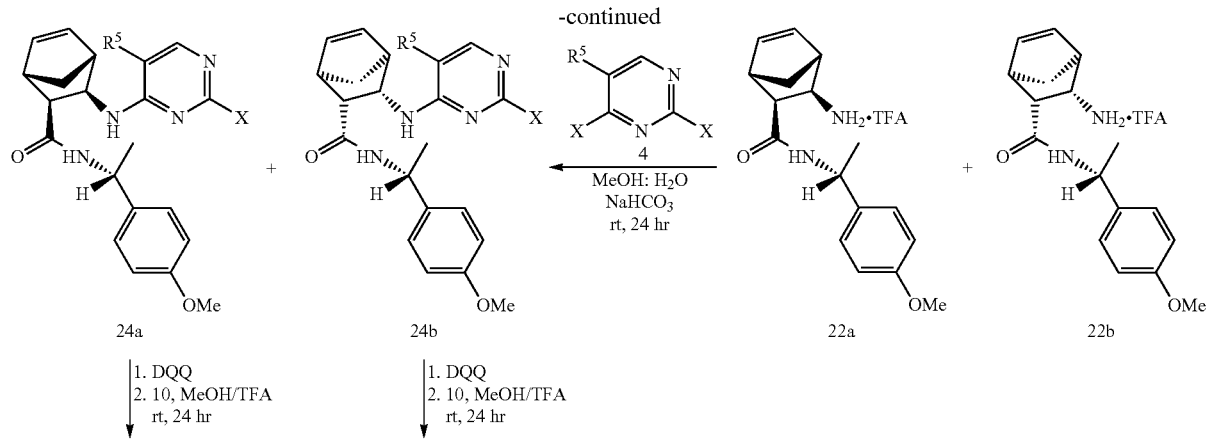

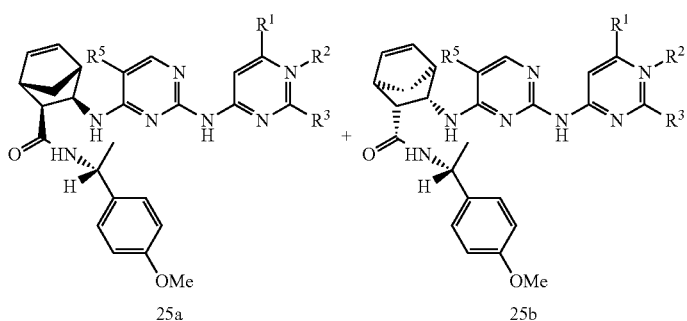

In Scheme (II), 2-exo-3-exo racemic β-lactam 14r1 (prepared as described in Stajar et al., 1984, Tetrahedron 40(12): 2385) is protected with a Boc group, yielding the corresponding racemic Boc-protected β-lactam 16r1. Boc-protected racemate 16r1 is then reacted with (R)-methyl-para-methoxybenzylamine 18, yielding a mixture of diastereomers 20a and 20b. This diastereomeric mixture is treated with an acid such as TFA to cleave the Boc group, yielding a mixture of diastereomers 22a and 22b, which can be reacted with 2,4-dihalopyrimidine 4 to afford a racemic mixture of compounds 24a and 24b. At this stage, compounds 24a and 24b can be separated from one another by crystallization and reacted with aniline 10 to afford isolated diastereomers 25a and 25b. The chiral auxiliaries from isolated diasteromers 25a and 25b can then be cleaved to yield isolated diastereomers according to structural formulae (Ia) and (Ib), respectively.

For compounds 25a and 25b in which $R^1$ is hydrogen, $R^2$ is 4-methyl-piperazin-1-yl, $R^3$ is methyl and $R^5$ is fluoro, cleavage of the chiral auxiliary proved difficult. For these and other compounds where such cleavage proves difficult, the chiral auxiliary can be cleaved from compounds 24a and 24b, and the resultant isolated compounds reacted with aniline 10 to yield isolated diastereomers according to structural formulae (Ia) and (Ib). Specific examples of such reactions are described in the Examples section.

Compounds that are stereoisomerically enriched, substantially stereoisomerically pure and/or stereoisomerically pure in specified diastereomers can also be synthesized from stereoisomerically enriched, substantially stereoisomerically pure, and/or stereoisomerically pure β-lactams. Such stereoisomerically enriched and/or (substantially) stereoisomerically pure β-lactams can be enzymatically resolved and isolated. In one exemplary embodiment, (substantially) stereoisomerically pure β-lactams can be resolved and isolated from a racemic mixture of 2-exo-3-exoβ-lactam 14r1 using an immobilized lipolase (available from Sigma Chemical Co., catalog no. L4777) as described in Eniko et al., 2004, Tetrahedron Asymmetry 15:573-575. In another exemplary embodiment, (substantially) stereoisomerically pure β-lactams can be resolved and isolated from 2-exo-3-exo Boc-protected racemic β-lactam 16r1 using resin bound, immobilized chirazyme L-2-type B, c.f. Enzyme (Candida antarctica Type B, c-f, available from Biocatalytics, Inc., Pasadena, Calif.) as described in application Ser. No. 60/628,401, filed Nov. 15, 2004, co-pending application Ser. No. 11/133,419 filed May 18, 2005, international application No. PCT/US05/17470 filed May 18, 2005, and co-pending application Ser. No. 11/281,186, entitled "Stereoisomerically Enriched β-Lactams Using Candida Antarctica," filed concurrently herewith, the disclosures of which are incorporated herein by reference. A specific example of the use of this enzyme is to resolve specified diastereomers of β-lactams is described in the Examples in section, as is a method of synthesizing 2-exo-3-exo racemic β-lactam 16r1.

Examples of synthesizing specified diasteromers according to structural formula (Ia) utilizing enzyme reactions are illustrated in Schemes (III) and (IV), below. A specific example of the use of Novozyme 435 enzyme as illustrated in Scheme (IV), which like the Chirazyme enyme discussed supra and illustrated in Scheme (III), can be used to resolve enantiomers from racemic β-lactams, is described in the Examples section.

Scheme (III)

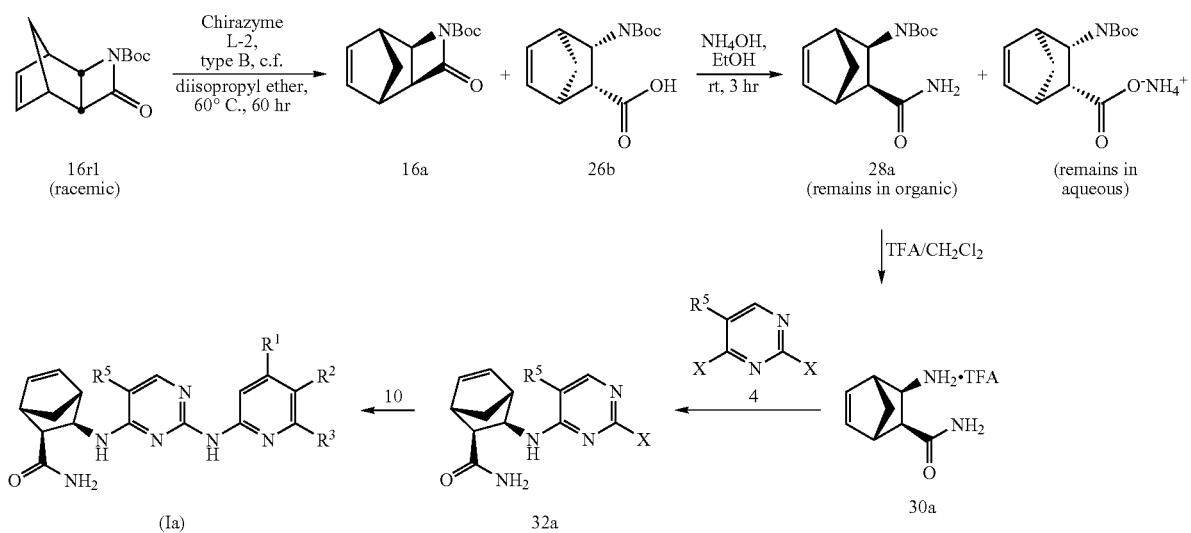

Scheme (IV)

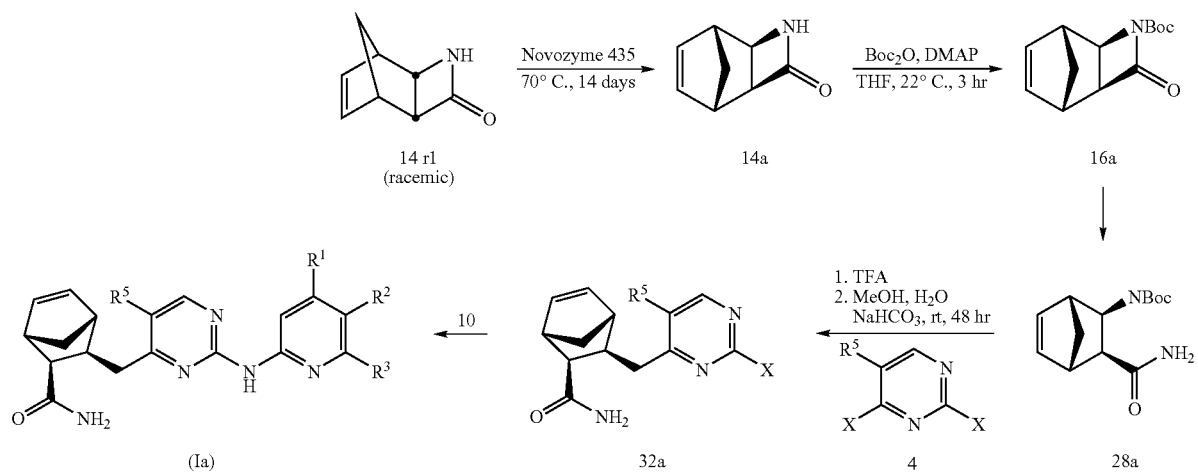

6.4 Activity of the Antiproliferative Compounds

Active stereoisomerically enriched compounds typically inhibit proliferation of desired cells, such as tumor cells, with an $IC_{50}$ in the range of about 20 µM or less, as measured in a standard in vitro cellular proliferation assay. Of course, skilled artisans will appreciate that compounds which exhibit lower $IC_{50}$s, for example on the order of 10 µM, 1 µM, 100 nM, 10 nM, 1 nM, or even lower, may be particularly useful in therapeutic applications. The antiproliferative activity may be cytostatic or it may be cytotoxic. In instances where antiproliferative activity specific to a particular cell type is desired, the compound may be assayed for activity with the desired cell type and counter-screened for a lack of activity against other cell types. The desired degree of "inactivity" in such counter screens, or the desired ratio of activity vs. inactivity may vary for different situations, and may be selected by the user.

Active compounds also typically inhibit an activity of an Aurora kinase, with an $IC_{50}$ in the range of about 20 µM or less, typically in the range of about 10 µM, 1 µM, 100 nM, 10 mM, 1 mM, or even lower. The $IC_{50}$ against an aurora kinase can be determined in a standard in vitro assay with an isolated aurora kinase, or in a functional cellular array. A suitable enzyme coupled assay that can be used to determine the degree of Aurora kinase activity is described in Fox et al., 1998, Protein Sci. 7:2249-2255. Kemptide peptide sequence LRRASLG (Bochern Ltd., UK) can be used as a substrate for Aurora kinase-A Aurora kinase-B and/or Aurora kinase-C, and reactions can be carried out at 30° C. in a solution containing 100 mM HEPES (pH 7.5), 10 mM Mg $Cl_2$, 25 mM NaCl, 1 mM DTT. $IC_{50}$ values can be determined using computerized non-linear regression with commercially-available software (e.g., Prism 3.0, GraphPed Software, San Diego, Calif.). A suitable cell-based functional assay is described in the Examples section.

6.5 Uses of the Antiproliferative Compounds

The active stereoisomerically enriched compounds, including the various prodrugs, salts, hydrates and/or N-oxide forms thereof, may be used to inhibit Aurora kinases, Aurora kinase-mediated processes, and/or cell proliferation in a variety of contexts. According to some embodiments, a cell or population of cells is contacted with an amount of such a compound effective to inhibit an activity of an Aurora kinase, an Aurora kinase-mediated process and/or proliferation of the cell or cell population. When used to inhibit cellular proliferation, the compound may act cytotoxically to kill the cell, or cytostatically to inhibit proliferation without killing the cell.

In some embodiments, the methods may be practiced in vivo as a therapeutic approach towards the treatment or prevention of Aurora kinase-mediated diseases or disorders, and in particular proliferative disorders. Thus, in a specific embodiment, the stereoisomerically enriched compounds described herein, (and the various forms described herein) may be used to treat or prevent proliferative disorders in animal subjects, including humans. The method generally comprises administering to the subject an amount of a stereoisomerically enriched compound, or a prodrug, salt, hydrate or N-oxide thereof, effective to treat or prevent the disorder. In one embodiment, the subject is a mammal, including, but not limited to, bovine, horse, feline, canine, rodent, or primate. In another embodiment, the subject is a human.

A variety of cellular proliferative disorders may be treated or prevented with the compounds described herein. In some embodiments, the compounds are used to treat various cancers in afflicted subjects. Cancers are traditionally classified based on the tissue and cell type from which the cancer cells originate. Carcinomas are considered cancers arising from epithelial cells while sarcomas are considered cancers arising from connective tissues or muscle. Other cancer types include leukemias, which arise from hematopoietic cells, and cancers of nervous system cells, which arise from neural tissue. For non-invasive tumors, adenomas are considered benign epithelial tumors with glandular organization while chondomas are benign tumor arising from cartilage. In the present invention, the described compounds may be used to treat proliferative disorders encompassed by carcinomas, sarcomas, leukemias, neural cell tumors, and non-invasive tumors.

In a specific embodiment, the compounds are used to treat solid tumors arising from various tissue types, including, but not limited to, cancers of the bone, breast, respiratory tract, brain, reproductive organs, digestive tract, urinary tract, bladder, eye, liver, skin, head, neck, thyroid, parathyroid, kidney, pancreas, blood, ovary, colon, germ/prostate, and mestastatic forms thereof.

Specific proliferative disorders include the following: a) proliferative disorders of the breast include, but are not limited to, invasive ductal carcinoma, invasive lobular carcinoma, ductal carcinoma, lobular carcinoma in situ, and metastatic breast cancer; b) proliferative disorders of the skin include, but are not limited to, basal cell carcinoma, squamous cell carcinoma, malignant melanoma, and Karposi's sarcoma; c) proliferative disorders of the respiratory tract include, but are not limited to, small cell and non-small cell lung carcinoma, bronchial edema, pleuropulmonary blastoma, and malignant mesothelioma; d) proliferative disorders of the brain include, but are not limited to, brain stem and hyptothalamic glioma, cerebellar and cerebral astrocytoma, medullablastoma, ependymal tumors, oligodendroglial, meningiomas, and neuroectodermal and pineal tumors; e) proliferative disorders of the male reproductive organs include, but are not limited to, prostate cancer, testicular cancer, and penile cancer f) proliferative disorders of the female reproductive organs include, but are not limited to, uterine cancer (endometrial), cervical, ovarian, vaginal, vulval cancers, uterine sarcoma, ovarian germ cell tumor; g) proliferative disorders of the digestive tract include, but are not limited to, anal, colon, colorectal, esophageal, gallbladder, stomach (gastric), pancreatic cancer, pancreatic cancer—Islet cell, rectal, small-intestine, and salivary gland cancers; h) proliferative disorders of the liver include, but are not limited to, hepatocellular carcinoma, cholangiocarcinoma, mixed hepatocellular cholangiocarcinoma, and primary liver cancer; i) proliferative disorders of the eye include, but are not limited to, intraocular melanoma, retinoblastoma, and rhabdomyosarcoma; j) proliferative disorders of the head and cancers include, but are not limited to, laryngeal, hypopharyngeal, nasopharyngeal, oropharyngeal cancers, and lip and oral cancer, squamous neck cancer, metastatic paranasal sinus cancer; k) proliferative disorders of the lymphomas include, but are not limited to, various T cell and B cell lymphomas, non-Hodgkins lymphoma, cutaneous T cell lymphoma, Hodgkins disease, and lymphoma of the central nervous system; l) leukemias include, but are not limited to, acute myeloid leukemia, acute lymphoblastic leukemia, chronic lymphocytic leukemia, chronic myelogenous leukemia, and hair cell leukemia, m) proliferative disorders of the thyroid include thyroid cancer, thymoma, and malignant thymoma; n) sarcomas include, but are not limited to, sarcoma of the soft tissue, osteosarcoma, malignant fibrous histiocytoma, lymphosarcoma, and rhabdomyosarcoma.

It is to be understood that the descriptions of proliferative disorders is not limited to the conditions described above, but encompasses other disorders characterized by uncontrolled growth and malignancy. It is further understood that proliferative disorders include various metastatic forms of the tumor and cancer types described herein. The compounds of the present invention may be tested for effectiveness against the disorders described herein, and a therapeutically effective regimen established. Effectiveness, as further described below, includes reduction or remission of the tumor, decreases in the rate of cell proliferation, or cytostatic or cytotoxic effect on cell growth.

6.6 Combination Therapies

The stereoisomerically enriched compounds described herein may be used alone, in combination with one another, or as an adjunct to, or in conjunction with, other established antiproliferative therapies. Thus, the compounds may be used with traditional cancer therapies, such as ionization radiation in the form of γ-rays and x-rays, delivered externally or internally by implantation of radioactive compounds, and as a follow-up to surgical removal of tumors.

In another aspect, the compounds may be used with other chemotherapeutic agents useful for the disorder or condition being treated. These compounds may be administered simultaneously, sequentially, by the same route of administration, or by a different route.

In some embodiments, the present compounds are used with other anti-cancer or cytotoxic agents. Various classes of anti-cancer and anti-neoplastic compounds include, but are not limited to, alkylating agents, antimetabolites, vinca alkyloids, taxanes, antibiotics, enzymes,. cytokines, platinum coordination complexes, substituted ureas, tyrosine kinase inhibitors, hormones and hormone antagonists. Exemplary alkylating agents include, by way of example and not limitation, mechlorothamine, cyclophosphamide, ifosfamide, melphalan, chlorambucil, ethyleneimines, methylmelamines, alkyl sulfonates (e.g., busulfan), and carmustine. Exemplary antimetabolites include, by way of example and not limitation, folic acid analog methotrexate; pyrimidine analog fluorouracil, cytosine arbinoside; purine analogs mecaptopurine, thioguanine, and azathioprine. Exemplary vinca alkyloids include, by way of example and not limitation, vinblastine, vincristine, paclitaxel, and colchicine. Exemplary antibiotics include, by way of example and not limitation, actinomycin D, daunorubicin, and bleomycin. An exemplary enzyme effective as anti-neoplastic agents include L-asparaginase. Exemplary coordination compounds include, by way of example and not limitation, cisplatin and carboplatin. Exemplary hormones and hormone related compounds include, by way of example and not limitation, adrenocorticosteroids prednisone and dexamethasone; aromatase inhibitors amino glutethimide, formestane, and anastrozole; progestin compounds hydroxyprogesteron caproate, medroxyprogesterone; and anti-estrogen compound tamoxifen.

These and other useful anti-cancer compounds are described in *Merck Index,* 13th Ed. (O'Neil M. J. et al., ed) Merck Publishing Group (2001) and *Goodman and Gilmans The Pharmacological Basis of Therapeutics,* 10th Edition, Hardman, J. G. and Limbird, L. E. eds., pg. 1381-1287, McGraw Hill, (1996), both of which are incorporated by reference herein.

Additional anti-proliferative compounds useful in combination with the stereoisomerically enriched compounds described herein include, by way of example and not limitation, antibodies directed against growth factor receptors (e.g., anti-Her2); antibodies for activating T cells (e.g., anti-CTLA-4 antibodies); and cytokines such as interferon-α and interferon-γ, interleukin-2 and GM-CSF.

6.7 Formulations and Administration

When used to treat or prevent such diseases, the active compounds and prodrugs may be administered singly, as mixtures of one or more active compounds, or in mixture or combination with other agents useful for treating such diseases and/or the symptoms associated with such diseases. The active compounds and prodrugs may also be administered in mixture or in combination with agents useful to treat other disorders or maladies, such as steroids, membrane stabilizers. The active compounds or prodrugs may be administered per se, or as pharmaceutical compositions comprising an active compound or prodrug.

Pharmaceutical compositions comprising the active compounds (or prodrugs thereof) may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the active compounds into preparations which can be used pharmaceutically (see Remington's *Pharmaceutical Sciences,* 15$^{th}$ Ed., Hoover, J. E. ed., Mack Publishing Co. (2003)

The active compound or prodrug may be formulated in the pharmaceutical compositions per se, or in the form of a hydrate, solvate, N-oxide or pharmaceutically acceptable salt, as previously described. Typically, such salts are more soluble in aqueous solutions than the corresponding free acids and bases, but salts having lower solubility than the corresponding free acids and bases may also be formed.

Pharmaceutical compositions may take a form suitable for virtually any mode of administration, including, for example, topical, ocular, oral, buccal, systemic, nasal, injection, transdermal, rectal, vaginal, etc., or a form suitable for administration by inhalation or insufflation.

For topical administration, the active compound(s) or prodrug(s) may be formulated as solutions, gels, ointments, creams, suspensions, etc. as are well-known in the art.

Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampoules or in multidose containers, and may contain added preservatives.

Alternatively, the injectable formulation may be provided in powder form for reconstitution with a suitable vehicle, including but not limited to sterile pyrogen free water, buffer, dextrose solution, etc., before use. To this end, the active compound(s) may be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate, lecithin). The tablets may be coated by methods well known in the art with, for example, sugars, films or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the active compound or prodrug, as is well known in the art.

For buccal administration, the compositions may take the form of tablets or lozenges formulated in conventional manner.

For rectal and vaginal routes of administration, the active compound(s) may be formulated as solutions (for retention enemas) suppositories or ointments containing conventional suppository bases such as cocoa butter or other glycerides.

For nasal administration or administration by inhalation or insufflation, the active compound(s) or prodrug(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

For ocular administration, the active compound(s) or prodrug(s) may be formulated as a solution, emulsion, suspension, etc. suitable for administration to the eye. A variety of vehicles suitable for administering compounds to the eye are known in the art. Specific non-limiting examples are described in U.S. Pat. Nos. 6,261,547; 6,197,934; 6,056,950; 5,800,807; 5,776,445; 5,698,219; 5,521,222; 5,403,841; 5,077,033; 4,882,150; and 4,738,851.

For prolonged delivery, the active compound(s) or prodrug(s) can be formulated as a depot preparation for administration by implantation or intramuscular injection. The active ingredient may be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption may be used. To this end, permeation enhancers may be used to facilitate transdermal penetration of the active compound(s). Suitable transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475.

Alternatively, other pharmaceutical delivery systems may be employed. Liposomes and emulsions are well-known examples of delivery vehicles that may be used to deliver active compound(s) or prodrug(s). Certain organic solvents such as dimethylsulfoxide (DMSO) may also be employed, although usually at the cost of greater toxicity.

The pharmaceutical compositions may, if desired, be presented in a pack or dispenser device which may contain one or more unit dosage forms containing the active compound(s). The pack may, for example, comprise metal or plastic foil, such as a blister pack. The pack or dispenser device may be accompanied by instructions for administration.

6.8 Effective Dosages

The active compound(s) or prodrug(s), or compositions thereof, will generally be used in an amount effective to achieve the intended result, for example in an amount effective to treat or prevent the particular disease being treated. The compound(s) may be administered therapeutically to achieve therapeutic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. Therapeutic benefit also includes halting or slowing the progression of the disease, regardless of whether improvement is realized.

The amount of compound administered will depend upon a variety of factors, including, for example, the particular indication being treated, the mode of administration, the severity of the indication being treated and the age and weight of the patient, the bioavailability of the particular active compound, etc. Determination of an effective dosage is well within the capabilities of those skilled in the art.

Effective dosages may be estimated initially from in vitro assays. For example, an initial dosage for use in animals may be formulated to achieve a circulating blood or serum concentration of active compound that is at or above an $IC_{50}$ of the particular compound as measured in an in vitro assay, such as the in vitro assays described in the Examples section. Calculating dosages to achieve such circulating blood or serum concentrations taking into account the bioavailability of the particular compound is well within the capabilities of skilled artisans. For guidance, the reader is referred to Fingl & Woodbury, "General Principles," *In: Goodman and Gilman's The Pharmaceutical Basis of Therapeutics*, Chapter 1, pp. 1-46, latest edition, Pergamon Press, and the references cited therein.

Initial dosages may also be estimated from in vivo data, such as animal models. Animal models useful for testing the efficacy of compounds to treat or prevent the various diseases described above are well-known in the art. Dosage amounts will typically be in the range of from about 0.0001 or 0.001 or 0.01 mg/kg/day to about 100 mg/kg/day, but may be higher or lower, depending upon, among other factors, the activity of the compound, its bioavailability, the mode of administration and various factors discussed above. Dosage amount and interval may be adjusted individually to provide plasma levels of the compound(s) which are sufficient to maintain therapeutic or prophylactic effect. For example, the compounds may be administered once per week, several times per week (e.g., every other day), once per day or multiple times per day, depending upon, among other things, the mode of administration, the specific indication being treated and the judgment of the prescribing physician. In cases of local administration or selective uptake, such as local topical administration, the effective local concentration of active compound(s) may not be related to plasma concentration. Skilled artisans will be able to optimize effective local dosages without undue experimentation.

Preferably, the compound(s) will provide therapeutic or prophylactic benefit without causing substantial toxicity. Toxicity of the compound(s) may be determined using standard pharmaceutical procedures. The dose ratio between toxic and therapeutic (or prophylactic) $LD_{50}/ED_{50}$ effect is the therapeutic index ($LD_{50}$ is the dose lethal to 50% of the population and $ED_{50}$ is the dose therapeutically effective in 50% of the population). Compounds(s) that exhibit high therapeutic indices are preferred.

6.9 Kits

The compounds and/or prodrugs described herein may be assembled in the form of kits. In some embodiments, the kit provides the compound(s) and reagents to prepare a composition for administration. The composition may be in a dry or lyophilized form, or in a solution, particularly a sterile solution. When the composition is in a dry form, the reagent may comprise a pharmaceutically acceptable diluent for preparing a liquid formulation. The kit may contain a device for administration or for dispensing the compositions, including, but not limited to syringe, pipette, transdermal patch, or inhalant.

The kits may include other therapeutic compounds for use in conjunction with the compounds described herein. In some embodiments, the therapeutic agents are other anti-cancer and anti-neoplastic compounds. These compounds may be provided in a separate form, or mixed with the compounds of the present invention.

The kits will include appropriate instructions for preparation and administration of the composition, side effects of the compositions, and any other relevant information. The instructions may be in any suitable format, including, but not limited to, printed matter, videotape, computer readable disk, or optical disc.

7. EXAMPLES

The inventions are further defined by reference to the following examples, which describe the preparation of the various compounds described herein, methods for assaying their biological activity, and methods for their use. It will be apparent to the skilled artisan that many modifications, both to the materials and methods may be practiced without departing from the scope of the inventions.

7.1 Preparation of 4(4Methylpiperazin-1-yl)-3-Methylinitrobenzene

Reaction:

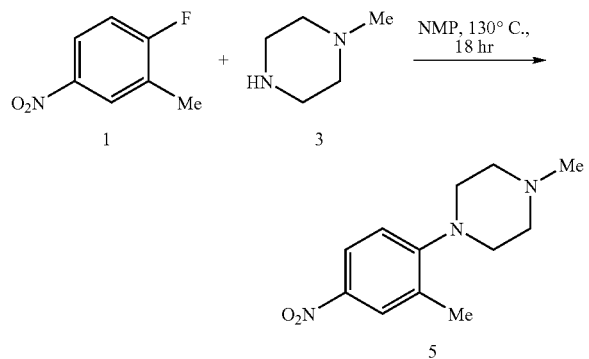

Procedure: A homogeneous mixture of 4-fluoro-3-methylnitrobenzene 1 (20 g, 129 mmol) and N-methylpiperazine 3 (25.82 g, 258 mmol) in N-methylpyrrolidone (NMP) (10 mL) was refluxed (120° C.) under $N_2$ for 24 hours. The reaction mixture upon cooling to room temperature was poured over a saturated NaCl solution (100 mL). The resulting solid was sonicated for approx. 30 seconds, filtered, washed with ice-cold water (2×10 mL) and dried under high vacuum to obtain 4-(4-methylpiperazin-1-yl)-3-methylnitrobenzene 5 (28 g, 92%). $^1$H NMR (CD$_3$OD): δ 8.02 (m, 2H), 7.13 (d, 1H, J=9.3 Hz), 3.08 (m, 4H), 2.66 (m, 4H), 2.38 (s, 6H); LCMS: purity: 99%, MS (m/e): 236 (MH$^+$).

7.2 Preparation of 4(4Methylpiperazin-1-yl)-3-Methylaniline

Reaction:

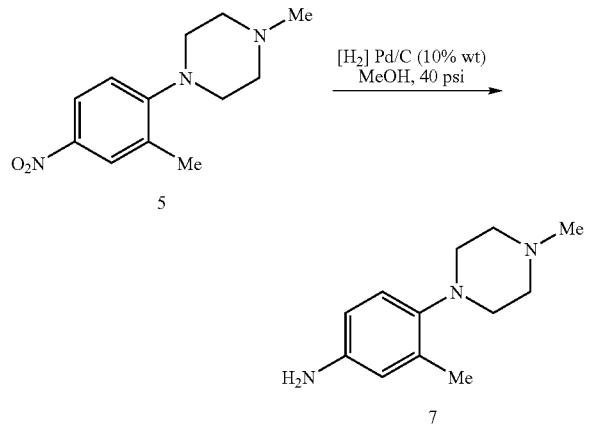

Procedure: A heterogeneous mixture of 4-(4-methylpiperazinyl)-3-methylnitrobenzene 5 (20 g, 85 mmol), 10% Pd/C (1.3 g) in methanol (1.2 liter) was hydrogenated [H$_2$] at 40 PSI for 3 hours. The palladium catalyst was filtered through a pad of celite, washed with methanol (3×50 mL) and the combined filtrate was concentrated to afford 4-(4-methylpiperazin-1-yl)-3-methylaniline 7 (15 g, 86%). $^1$H NMR (CD$_3$OD): δ 6.83 (d, 1H, J=8.7 Hz), 6.59 (d, 1H, J=2.7 Hz), 6.54 (dd, 1H, J=8.4 and 2.7 Hz), 2.84 (t, 4H, J=4.8 Hz), 2.60 (bm, 4H), 2.34 (s, 3H), 2.20 (s, 3H); LCMS: purity: 99.9%, MS (m/e): 206 (MH$^+$).

7.3 Preparation of 3-Aza-4-oxo-tricyclo[4.2.1.0(2,5)]non-7-ene

Reaction:

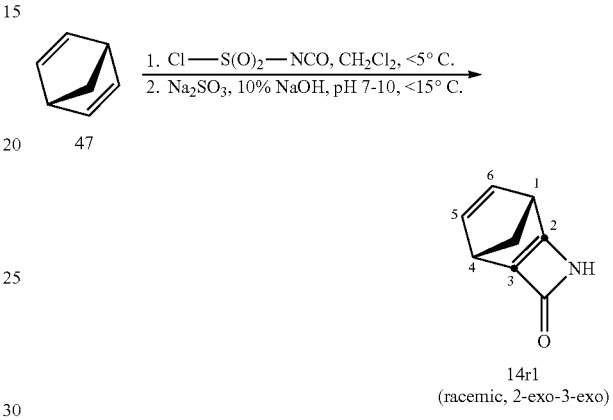

Procedure: Part 1: A solution of 2,5-norbornadiene 47 (25.0 mL, 0.246 mole) in CH$_2$Cl$_2$ (110 mL, fresh bottle) was cooled in an ice/NaCl bath (–10° C.). To this was added drop-wise a solution of CSI (21.4 mL, 0.246 mole) in CH$_2$Cl$_2$ (45 mL, fresh bottle) at a rate to maintain the temperature below 5° C. (the addition took approx. 1.25 hr.). Upon completion of the addition, the reaction mixture was stirred for 1 hour at 0-5° C. and then removed from the cooling bath and allowed to warm to 20° C. The reaction mixture was quenched with water (60 mL) and vigorously stirred for several minutes. The organic layer was separated, washed with brine, and dried with Na$_2$SO$_4$. Concentration gave light brown oil.

Part 2: A mixture of Na$_2$SO$_3$ (24.5 g), water (70 mL), and CH$_2$Cl$_2$ (30 mL) was cooled in an ice/NaCl bath. The oil from Part 1 was diluted to 100 mL with CH$_2$Cl$_2$ and added drop-wise to the above mixture at a rate to maintain the temperature below 15° C. (the addition took approx. 1.75 hr). The pH of the reaction mixture was monitored with a pH meter and kept basic (pH 7-10) by adjusting with 10% NaOH (w/v) (as needed). Upon completion of the addition, the reaction mixture was stirred for 1 hour at 5-10° C. (final pH was 8.5). The reaction mixture was poured into a separatory funnel and the CH$_2$Cl$_2$ layer separated. This organic phase was a thick and gelatinous solid suspension. It was diluted with water (approx. 400 mL) to make a more free flowing solution. The aqueous layer was further extracted with CH$_2$Cl$_2$ (4×100 mL). (Alternatively, the solids can be separated from the CH$_2$Cl$_2$ by centrifugation. The solids can then be diluted with water (until almost all dissolved) and extracted with CH$_2$Cl$_2$). The aqueous layer was further extracted with CH$_2$Cl$_2$ (10× 100 mL). The CH$_2$Cl$_2$ extracts were monitored by TLC for the presence of product. The combined organic extracts were washed with brine, dried with MgSO$_4$, and filtered through celite. Removal of solvent gave the desired product, racemic-2-exo-3-endo 3-aza-4-oxo-tricyclo[4.2.1.0(2,5)]non-7-ene 14r1 as white solid (20.5 g, 62%). $^1$H NMR (DMSO-$d_6$): δ 8.01 (bs, 1H), 6.22 (dd, J=3.3 and 5.4 Hz, 1H), 6.12 (dd, J=3.3 and 5.4 Hz, 1H), 2.88 (dd, J=1.5 and 3.3, 1H), 2.79 (bs, 1H), 2.74 (bs, 1H), 1.58 (d, J=9.3 Hz, 1H), and 1.47 (d, J=9.3 Hz, 1H).

7.4 Preparation of 4-Oxo-3-tert-butoxycarbonylaza-tricyclo[4.2.1.0(2,5)]non-7-ene Reaction:

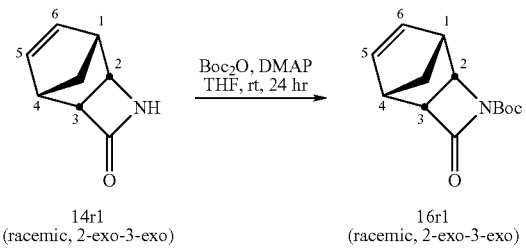 [SMILES: O=C1N[C@@H]2[C@H]1[C@@H]1C=C[C@H]2C1 ; CC(C)(C)OC(=O)N1C(=O)[C@H]2[C@@H]1[C@H]1C=C[C@@H]2C1]

Procedure: A homogeneous mixture of 3-aza-4-oxo-tricyclo[4.2.1.0(2,5)]non-7-ene (14r1; racemic-2-exo-3-exo; 10.0 g, 74 mmol), (BOC)$_2$O (16.1 g, 74 mmol) and DMAP (1.1 g) in CH$_2$Cl$_2$ was stirred under N$_2$ at room temperature for 24 hours. To this reaction mixture were added EtOAc (100 mL) followed by H$_2$O (100 mL) and stirred for additional 1 hour. The organic layer was separated and washed with H$_2$O (2×100 mL). The organic layer was dried over anhydrous Na$_2$SO$_4$ and solvent was removed under a reduced pressure to afford 4-oxo-3-tert-butoxycarbonylaza-tricyclo[4.2.1.0(2,5)]non-7-ene (16r1; racemic-2-exo-3-exo) (16.5 g, 70%); $^1$H NMR (DMSO-$d_6$): δ 6.29 (dd, J=3.3 and 5.4 Hz, 1H), 6.19 (dd, J=3.3 and 5.4 Hz, 1H), 3.77 (d, J=4.5 Hz, 1H), 3.13 (bs, 1H), 3.08-3.04 (m, 1H), 2.93 (bs, 1H), 1.45 (s, 9H), LCMS: 95%.

7.5 Preparation of, and Isolation of, Stereoisomerically Pure Diastereomers From (±) Racemic (2-exo-3-exo)-N4-(3-aminocarbonylbicyclo[2.2.1]hept-5-en-2-yl)-5-fluoro-N2-[3-methyl-4-(4-methylpiperazin-1-yl)phenyl]-2,4-pyrimidinediamine A racemic mixture of the title compound was prepared from the 2-exo-3-exo racemate of 2-aminobicylco[2.2.1]hept-5-ene-3-carboxamide as follows.

Reaction:

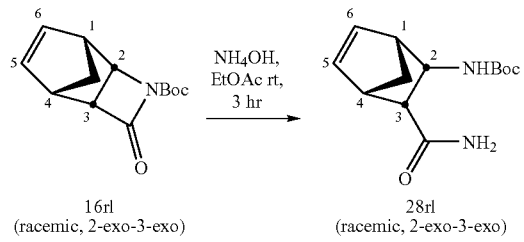 [SMILES: CC(C)(C)OC(=O)N1C(=O)[C@H]2[C@@H]1[C@H]1C=C[C@@H]2C1 ; CC(C)(C)OC(=O)N[C@@H]1[C@H](C(N)=O)[C@@H]2C=C[C@H]1C2]

Procedure: A round bottom flask equipped with a rubber septum and a magnetic stirring bar was charged with racemic N-BOC-β-lactam 16r1 (2.0 g) under a positive pressure of nitrogen. To this were added ethyl acetate (25 mL) followed by 30% ammonia in water (25 mL) and stirred at room temperature for 3 hours. The ethyl acetate layer was separated and washed with 5% aqueous solution of NaHCO$_3$ (20 mL), dried over anhydrous Na$_2$SO$_4$ and solvent was evaporated to afford 1.10 gm of racemic N-BOC carboxyamide 28r1.

Reaction:

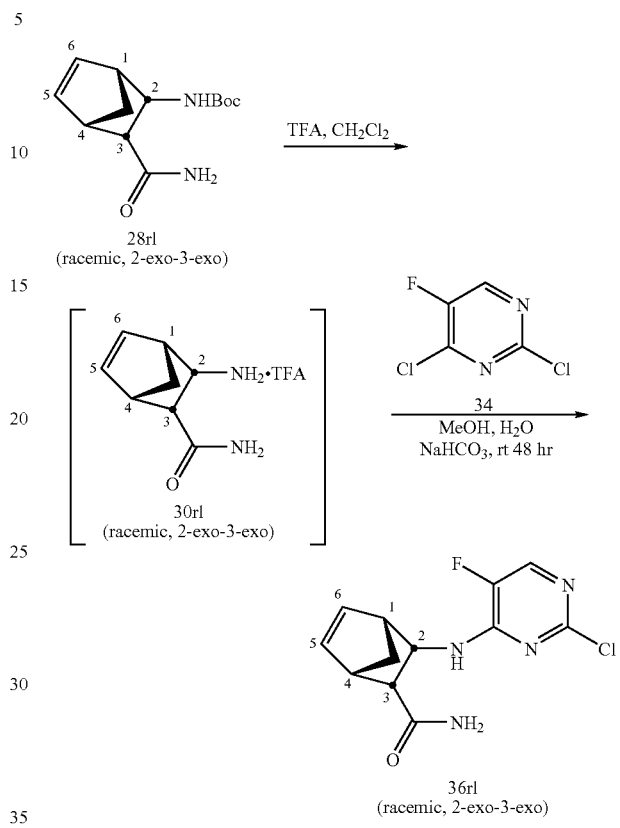

Procedure: A round bottom flask equipped with N$_2$ inlet and a magnetic stirring bar was charged with racemic N-BOC lactam 28r1 (2.00 g, 7.9 mmol) and then treated with 20% of TFA in CH$_2$Cl$_2$ at room temperature for 2 hours. The resulting solution was concentrated under a reduced pressure. The trace of TFA was removed under high vacuum for several hours to afford the intermediate, TFA salt (30r1, racemic). The resulting racemic TFA salt 30r1 was treated with 2,4-dichloro-5-fluoropyrimidine 10 (1.58 g, 9.51 mm) in MeOH:H$_2$O (20:10 mL) in the presence of NaHCO$_3$ (1.33 g, 15.84 mmol) at room temperature for 48 hours. The reaction mixture was diluted with H$_2$O (25 mL), saturated with NaCl and extracted with EtOAc (3×50 mL). Upon drying over anhydrous Na$_2$SO$_4$, the solvent was evaporated and the residue was chromatographed (silica gel, CH$_2$Cl$_2$ then 2-4% 2N NH$_3$/MeOH in CH$_2$Cl$_2$) to afford 1.3 g of racemic mono-SNAr product 36r1.

Reaction:

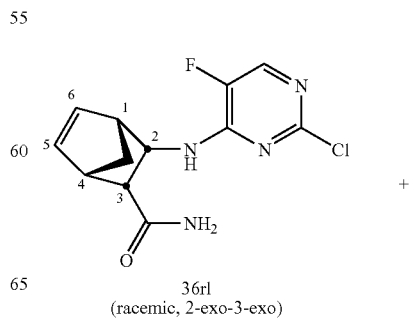

+

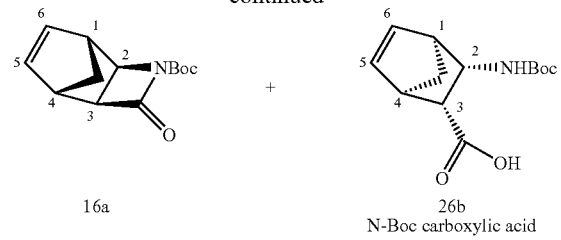

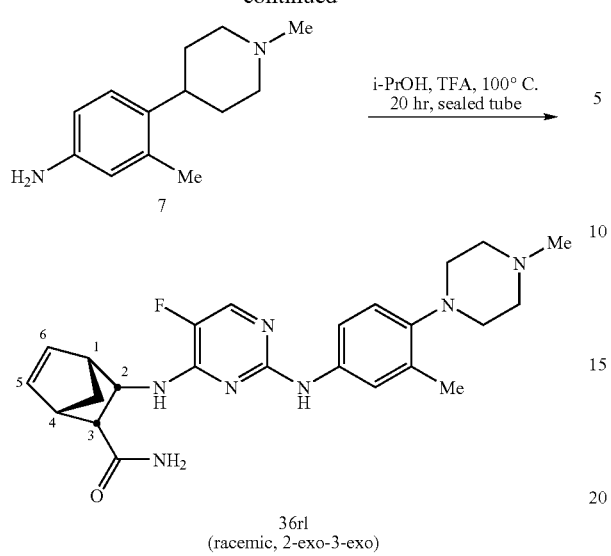

36r1
(racemic, 2-exo-3-exo)

Procedure: A sealed tube charged with racemic mono-SNAr product 36r1 (1.1 g, 8 mmol), aniline 7 (0.90 g, 4.4 mmol), TFA (0.6 mL) and methanol (9 mL) was stirred at 100° C. for 24 hours. The resulting viscous homogeneous solution was concentrated and the residue was chromatographed (silica gel, CH$_2$Cl$_2$ then 2-5% 2N NH$_3$/MeOH in CH$_2$Cl$_2$) to afford the expected 2-exo-3-exo racemic 2,4-pyrimidinediamine derivative 60r1 (1.12 g; purity: 95%):

Isolation of Enantionmers: The diastereomers were resolved and isolated from racemate 60r1 by chiral preparative HPLC chromatography Phenomenex Chirex 3020 250× 10 mm column), eluting with a 35:63:2 (vol:vol:vol) mixture of hexane:dichloromethane:methanol at a flow rate of 6mL/min. The enantiomer eluting at 9.44 min. was designated the E1 enantiomer and the enantiomer eluting at 12.74 min. was designated the E2 enantiomer.

7.6 Enzymatic Preparation of Stereoisomerically Pure (1R,2R,3S,4S)-N4-(3-Aminocarbonylbicyclo[2.2.1]hept-5en-2-yl)-5fuoro-N2-[3-methyl-4(4-methylpiperazin-1-yl)phenyl]-2,4pyrimidinediamine Using Chirazyme

7.6.1 Preparation of Stereochemically Pure N-Boc-β-Lactam

Reaction:

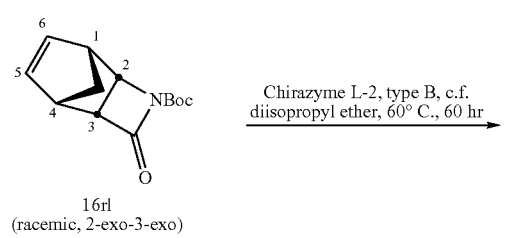

16r1
(racemic, 2-exo-3-exo)

Procedure: A dry sealed tube charged with 4-oxo-3-tert-butoxycarbonylaza-tricyclo[4.2.1.0(2,5)]non-7-ene (16r1; racemic-2-exo-3-exo) (4.0 g, 17.02 mmol), resin bound/immobilized chirazyme L-2, type B, c.f. (8.0 g, purchased from BioCatalytics Inc., Pasadena, Calif.) and diisopropyl ether (80 mL) was gently shaken in an incubator at 60° C. for 60 hours. (The enzymatic resolution of racemic N-BOC β-lactam 16r1 was followed by proton NMR. The integration of tert-butyl group of enantiomerically pure N-BOC lactam 16a and N-BOC carboxylic acid 26b was seen in 1:1 ratio). The resulting reaction mixture was filtered and the solid resin was washed with diisopropyl ether (2×40 mL). The filtrate was concentrated to afford a mixture of enatiomerically pure N-BOC-β-lactam 16a and N-BOC carboxylic acid 26b (total mass: 4.0 gm).

Reaction:

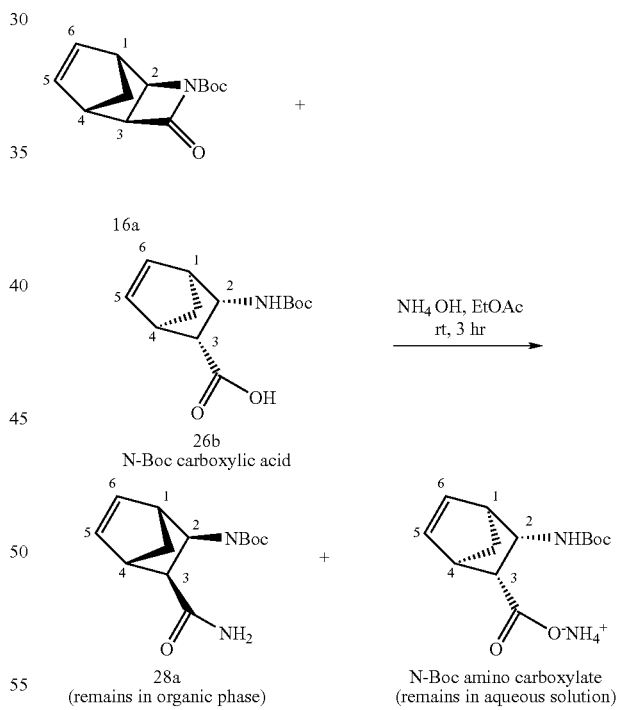

Procedure: A round bottom equipped with a rubber septum and a magnetic stirring bar was charged with a mixture of enantiomerically pure N-BOC-lactam 16a and N-BOC carboxylic acid 26b (4.0 g) under a positive pressure of nitrogen. To this were added ethyl acetate (50 mL) followed by 25% aqueous ammonium hydroxide (50 mL) and stirred at room temperature for 3 hours. The reaction progress was monitored by TLC. The ethyl acetate layer was separated and washed with 5% aqueous solution of NaHCO$_3$ (40 mL), dried over anhydrous Na$_2$SO$_4$ and solvent was evaporated to afford 2.00 gm (7.93 mmol out of a theoretical 8.51 mmol; 93% yield) of the desired enantiomerically pure N-BOC carboxamide 28a with greater than 99% enantiomeric excess, as determined by chiral HPLC. The aqueous solution containing the N-BOC ammonium carboxylate upon acidification with cold 1N HCl followed by extraction with CH$_2$Cl$_2$ regenerated the N-BOC carboxylic acid 26b (1.8 g, 7.11 mmol out of a theoretical 8.51 mmol, 84% yield). $^1$H NMR (DMSO-d6): 7.26 (bs, 1H), 6.66 (bs, 1H), 6.13 (m, 2H), 3.59 (t, 1H, J=6.9 Hz), 2.80 (s, 1H), 2.54 (s, 1H), 2.31 (d, 1H, J=8.1 Hz), 2.00 (d, 1H, J=8.7 Hz), 1.36 (s, 9H), 1.30 (d, 1H, J=8.1 Hz); LCMS: MS (m/z): 254 (MH$^+$); [α]$_D$ −76.78° (c 1.0, MeOH).

7.6.2 Preparation of Stereoisomerically Pure Mono SNAr Product

Reaction:

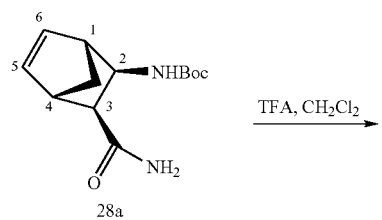

Procedure: A round bottom flask equipped with N$_2$ inlet and a magnetic stirring bar was charged with enantiomerically pure N-BOC carboxyamide 28a (2.00 g, 7.93 mmol) and then treated with 20% of TFA in CH$_2$Cl$_2$ at room temperature for 2 hours. The reaction progress was monitored by TLC. The resulting solution was concentrated under a reduced pressure. The trace of TFA was removed under high vacuum for several hours to afford the enantiomerically pure intermediate, TFA salt 30a in quantitative yield. $^1$H NMR (DMSO-d6): 8.10 (bs, 2H), 7.92 (s, 1H), 7.25 (s, 1H), 6.29 (m, 1H), 6.18 (m, 1H), 4.38 (bs, 1H), 3.06 (d, 1H, J=7.2 Hz), 2.97 (s, 1H), 2.87 (s, 1H), 2.43 (d, 1H, J=7.5 Hz), 2.10 (d, 1H, J=6 Hz), 1.36 (d, 1H, J=8.7 Hz); LCMS: MS (m/z): 152 (MH$^+$).

The resulting TFA salt 30a was treated with 2,4-dichloro-5-fluoropyrimidine 34 (1.58 g, 9.51 mmol) in MeOH:H$_2$O (20:10 mL) in the presence of NaHCO$_3$ (1.33 g, 15.84 mmol) at room temperature for 48 hours. The reaction mixture was diluted with H$_2$O (25 mL), saturated with NaCl and extracted with EtOAc (3×50 mL). Upon drying over anhydrous Na$_2$SO$_4$ the solvent was evaporated and the residue was chromatographed (silica gel, CH$_2$Cl$_2$ then 2-4% 2N NH$_3$/MeOH in CH$_2$Cl$_2$) to afford 2.02 g (91%) of desired mono-SNAr product 36a $^1$H NMR (DMSO-d6): 8.25 (d, 1H, J=7.2 Hz), 8.07 (d, 1H, J=3.3 Hz), 7.71 (s, 1H), 7.19 (s, 1H), 6.29 (m, 2H), 3.99 (t, 1H, J=7.8 Hz), 2.85 (s, 1H), 2.75 (s, 1H), 2.49 (d, 1H, J=0.9 Hz), 2.11 (d, 1H, J=8.7 Hz), 1.39 (d, 1H, J=8.7 Hz); LCMS: purity: 95%, MS (m/z): 283 (MH$^+$). The enantiomeric purity was greater than 99% as determined by chiral HPLC; [α]$_D$ +61.10° (c 1.0, MeOH).

7.6.3 Preparation of Stereoisomerically Pure (1R,2R,3S,4S)-N4-(3-Aminocarbonylbicyclo[2.2.1]hept-5en-2-yl)-5-fluoro-N2-[3-methyl-4-(4-methylpiperazin-1-yl)phenyl]-2,4-pyrimidinediamine Reaction:

Procedure: A dry reaction flask equipped with a stirring bar, reflux condenser and an N$_2$ inlet was charged with enantiomerically pure mono-SNAr product 36a (2.25 g, 8 mmol), aniline 7 (1.80 g, 8.8 mmol), TFA (1.12 mL) and isopropanol (18 mL) and the resulting reaction mixture was stirred at reflux temperature for 8-10 hours. After cooling the reaction mixture to room temperature, ethyl acetate (20 mL) was added. The solid obtained was filtered and washed with ethyl acetate (2×5 mL) to afford compound 60a in the form of acidic salt. The resulting solid was then taken into water and the aqueous mixture adjusted to pH 9 with aqueous NaHCO$_3$, which caused precipitation of a solid. The solid was filtered from the mixture, washed with water and dried to give 3.3 g (93%) of 2,4-pyrimidinediamine derivative 60a. $^1$H NMR (DMSO-d6): 8.85 (s, 1H), 7.83 (d, 1H, J=2.7 Hz), 7.68 (s, 1H), 7.47 (s, 2H), 7.36 (d, 1H, J=7.8 Hz), 7.18 (s, 1H), 6.89 (d, 1H, J=8.7 Hz), 6.32 (m, 1H), 6.25 (m, 1H), 4.11 (t, 1H, J=7.8 Hz), 3.32 (s, 3H), 2.86 (s, 1H), 2.76 (m, 4H), 2.49 (m, 4H), 2.46 (m, 2H), 2.21 (s, 3H), 2.11 (d, 1H, J=8.4 Hz), 1.39 (d, 1H, J=9 Hz); LCMS: purity: 100%, MS (m/z): 452 (M$^+$); >99% ee as determined by chiral HPLC; $[\alpha]_D^{RT}$ +101.2° (c 1.0, MeOH). The chiral analytical data, $^1$H NMR and LCMS were found to be identical with the enantiomer designated E1.

7.7 Enzymatic Preparation of Stereoisomerically Pure (1R,2R,3S,4S)-N4-(3-Aminocarbonylbicyclo[2.2.1]hept-5-en-2-yl)-5-fluoro-N2-[3-methyl-4(4-methylpiperazin-1-yl)phenyl]-2,4-pyrimidinediamine Using Novazyme 435 Enzyme

7.7.1 Preparation of Stereoisomerically Pure β-Lactam

Reaction:

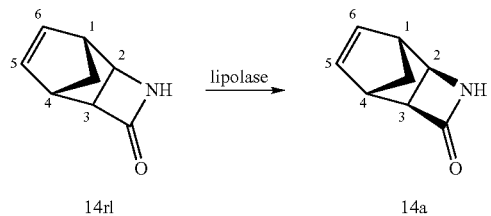 [SMILES: O=C1NC2C1[C@@H]1C=C[C@H]2C1 ; O=C1N[C@H]2[C@@H]1[C@@H]1C=C[C@H]2C1]

14rl          14a

Procedure: Immobilized Lipolase (8.0 g, from Sigma, order number L4777), β-lactam 14rl (racemic: 2-exo-3-exo) (4.0 g, 7.4 mmol) and water (0.13 ml, 7.4 mmol) were added to 250 ml diisopropyl ether in a pressure flask. The mixture was degassed with nitrogen for 20 minutes and the flask was sealed and incubated for 14 days at 70° C. The mixture was cooled to room temperature, filtered over celite and washed with 300 ml diisopropyl ether. The combined filtrate was concentrated to dryness and the residue was crystallized from diisopropyl ether to give the enantiomerically pure β-lactam 14a as colorless needles (1.22 g, 61%). The enantiomeric purity was greater than 99% as determined by chiral HPLC.

7.7.2 Preparation of Stereoisomerically Pure 2-N-Boc-amino-3-aminocarbonyl-bicyclo[2.2.1]hept-5-ene Reaction:

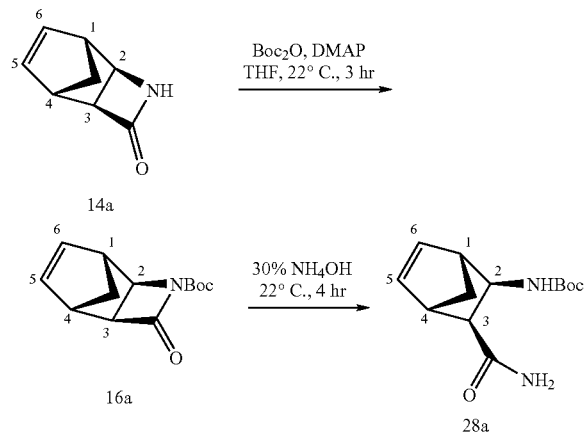

Procedure: A homogeneous mixture of enantiomerically pure 3-aza4-oxo-tricyclo[4.2.1.0(2,5)]non-7-ene 14a (1.1 g, 8.2 mmol), (BOC)$_2$O (2.76 g, 12.3 mmol (100 mg)) in CH$_2$Cl$_2$ was stirred under N$_2$ at room temperature for 3 hours to give enantiomerically pure N-BOC lactam 16a, which was used further without isolation. To this reaction mixture was added 20 ml of 25% aqueous ammonium hydroxide and stirring was continued for another 4 hours. Water was added and the reaction mixture was extracted with dichloromethane (2×50 ml). The combined organic phase was washed with aqueous HCl (5%), dried over sodium sulfate and reduced to dryness under reduced pressure to give enantiomerically pure N-BOC carboxyamide 28a (2.51 g) as a white solid, which was used in the next step without further purification.

7.7.3 Preparation of Stereoisomerically Pure Mono SNAr Product (1R,2R,3S,4S)-N4-(3-Aminocobonyl-bicyclo[2.2.1]hept-5-en-2-yl)-2-chloro-5-fluoro-4-aminopyridine Reaction:

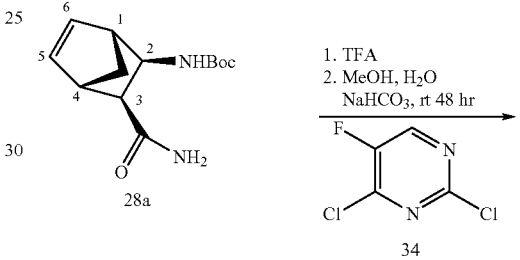

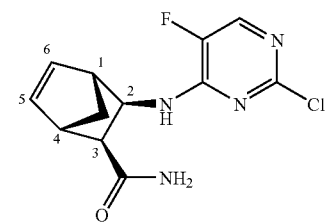

Procedure: The enatiomerically pure N-BOC carboxyamide 28a (2.51 g) was dissolved in 10 ml dichloromethane and treated with 10 ml TFA. The mixture was stirred for 1 hour at room temperature and concentrated to dryness under reduced pressure. The residue was suspended in toluene and again concentrated to dryness. The resulting solid was dissolved in methanol:water (30 ml:3 ml) and treated with 1.5 g sodium bicarbonate. The 5-fluoro-2,4-dichloropyrimidine 34 (3 g, 17.9 mmol) was added and the mixture was stirred for 2 days at room temperature. The volatiles were removed under vacuum and the residue was suspended in brine. The precipitate was filtered, dried and subjected to column chromatography (silica gel, dichloromethane-methanol, 20:1) to give the desired enantiomerically pure mono-SNAr product 36a as a white solid (1.7 g, 74%).

7.7.4 Preparation of Stereoisomerically Pure (1R,2R,3S,4S)-N4-(3-Aminocarbonylbicyclo[2.2.1]hept-5en-2-yl)-5fluoro-N2-[3-methyl-4-(4-methylpiperazin-1-yl)phenyl]-2,4-pyrimidinediamine Reaction:

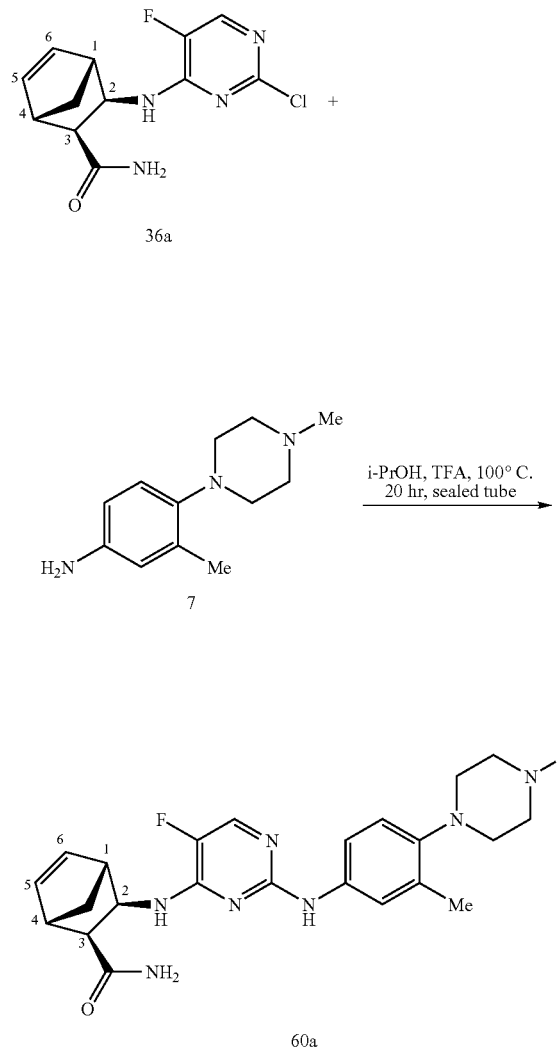

Procedure: A homogeneous mixture of aniline 7 (400 mg, 1.95 mmol), enantiomerically pure mono-SNAr product 36a (400 mg, 1.41 mmol) and 0.2 ml TFA in 4 ml isopropanol in a sealed tube was stirred at 100° C. for 20 hours. The mixture was cooled to room temperature, diluted with 2 ml diethylether and the resulting precipitate was filtered and washed with diethylether. The remaining solids were dissolved in water and treated with aqueous 25% ammonium hydroxide solution. The resulting precipitate was filtered, washed with water and dried to give 527 mg (83%) of desired product, 2,4-pyrimidindiamine derivative 60a as an off-white solid. Purity was determined by LCMS to be greater than 97% and the enantiomeric purity was determined by chiral HPLC to be greater than 99%. The chiral analytical data, $^1$H NMR and LCMS analyses were identical with the enantiomer that was designated E1.

7.8 Preparation of Stereoisomerically Pure Compounds Using (R)-Methyl-p-Methoxybenzylamine as a Chiral Auxiliary

7.8.1 Preparation of 2-Exo-3-Exo Racemic Amines

Reaction:

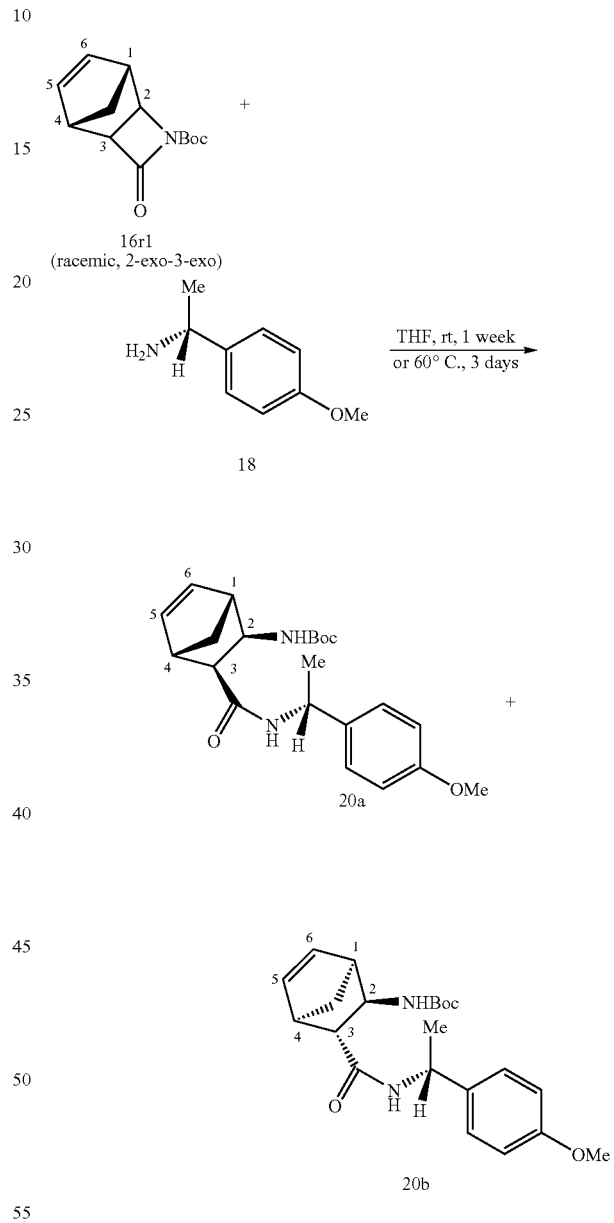

Procedure: A homogeneous mixture of 4-oxo-3-tert-butoxycarbonylaza-tricyclo[4.2.1.0(2,5)]non-7-ene (16r1; racemic-2-exo-3-exo) (9.2 g, 40 mmol) and (R)-methyl-4-methoxylbenzylamine 13 (18, 24 g, 48 mmol) in dry THF (75 mL) was stirred at room temperature for 48 hours. The reaction mixture was concentrated, suspended in hexanes (5 mL), sonicated and the solid was separated by filtration to give mixture of diasterisomers 20a and 20b (12 mg). Alternatively, the purification can be done using column chromatography (silica gel, hexanes then 5%, 10%, 20% and 50% EtOAc in hexanes).

7.8.2 Preparation of 2-Exo-3-Exo Racemic Mono SNAr Products Followed By Separation of Isomerically Pure Compounds by Crystallization Reaction:

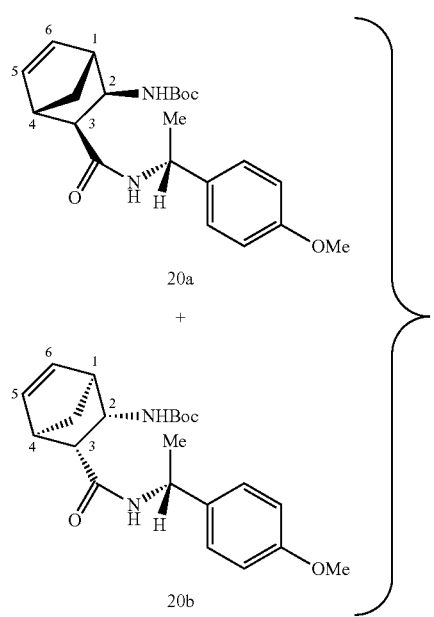

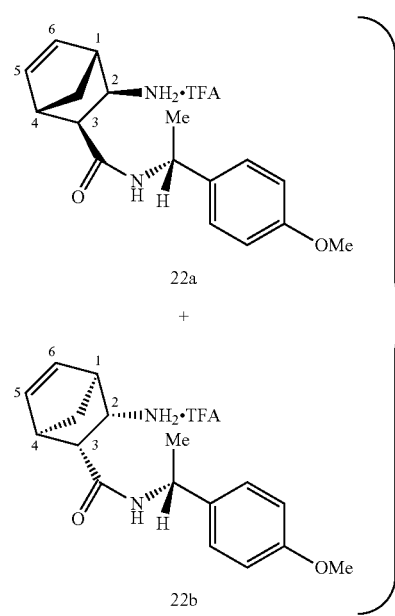

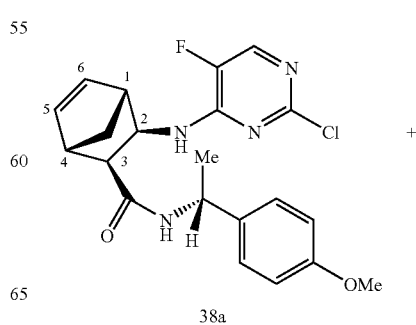

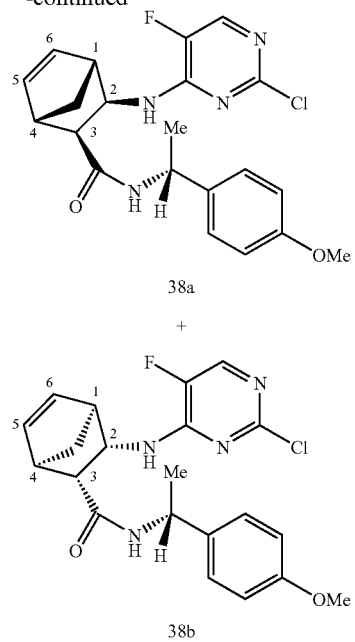

Procedure: A heterogeneous mixture of diasterisomers 20a and 20b (6.0 g g, 17 mmol), TFA (20 mL) in CH$_2$Cl$_2$ was stirred at room temperature for 2 hours. TLC was used to monitor the progress of the reaction. The resulting reaction was concentrated to dryness and dried under a high vacuum for several hours to afford a diasterisomericgg mixture of intermediates 22a and 22b. This mixture was then reacted with 2,4-dichloro-5-fluoropyrimidine 34 (3.4 g, 20 mmol) in the presence of NaHCO$_3$ (5.7 g, 68 mmol) in MeOH:H$_2$O (50 mL, each) at room temperature for 24 hours. The reaction mixture was then diluted with NaCl-saturated water (50 mL) and extracted with CH$_2$Cl$_2$. The extract upon drying over anhydrous Na$_2$SO$_4$ followed by removal of solvent under reduced pressure gave a residue, which was chromatographed (silica gel, CH$_2$Cl$_2$ then 2% 2N NH$_3$/MeOH in CH$_2$Cl$_2$). The chromatographic purification gave a mixture diasterisomers 38a and 38b (4.0 g) (1:1 ratio can be seen with a clear separation on reverse phase LCMS). The resulting 4.0 grams upon crystallization using EtOAc:hexanes (30:150 mL; v/v) afforded crystalline material of intermediate 38a, which was confirmed by X-ray crystal structure; chemical purity: 96% and % de: 96%. [α]$_D$ −36.7° (c, 0.18 MeOH). The mother liquor containing the other isomer had poor % de (70-80%), which is assumed to be diastereoisomer 38b.

7.8.3 Preparation of Stereoisomerically Pure Product Including the Chiral Auxiliary Reaction:

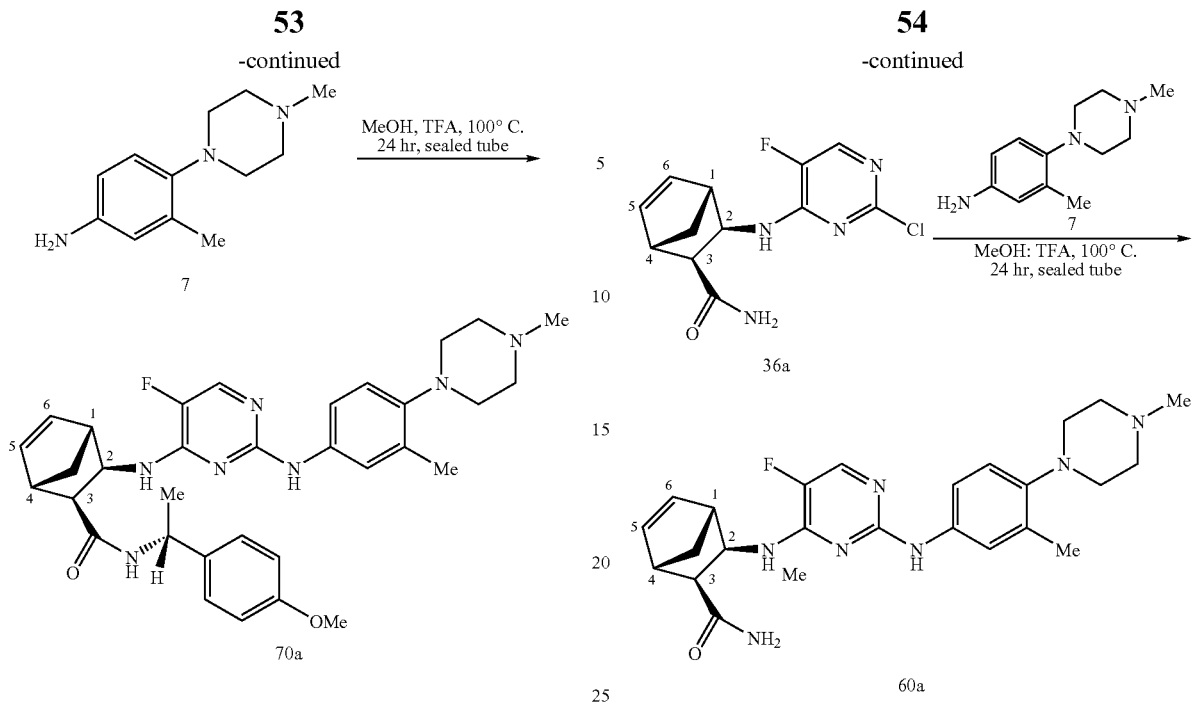

Procedure: A mixture of diastereoisomer 38a (1.42 g, 3.4 mmol), aniline 7 (0.834 g, 4.0 mmol) and TFA (700 mg) in MeOH (10 mL) was heated in a sealed tube at 100° C. for 24 hours. The resulting residue was chromatographed (silica gel, $CH_2Cl_2$ then 2% 2N $NH_3$/MeOH in $CH_2Cl_2$) to afford product 40a as colorless solid, chemical purity: 96%.

7.8.4 Cleavage of the Chiral Auxiliary

The cleavage of chiral auxiliary from 40a was found to be difficult, therefore the cleavage of chiral auxiliary from intermediate compounds 38a and 38b followed by the second SNAr reaction with aniline 7 was carried as follows.

7.8.5 Cleavage of the Chiral Auxiliary From Stereoisomerically Pure Intermediate 38a and Preparation of Stereoisomerically Pure (1R,2R,3S,4S)-N4-(3-Aminocarbonylbicyclo[2.2.1]hept-5-en-2-yl)-5-fluoro-N2-[3-methyl-4-(4-methylpiperazin-1-yl)phenyl]-2,4-pyrimidinediamine Reaction:

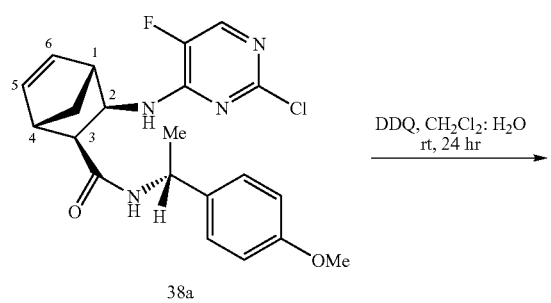

38a

Procedure: The mono-SNAr product with chiral auxiliary 38a was allowed to react with DDQ (3 equivalents) in $CH_2Cl_2$:$H_2O$ at room temperature to obtain the desired mono-SNAr product 36a. The mono-SNAr product was purified by column chromatography and found to be same as compound 36a obtained via enzymatic route, which was confirmed by chiral analytical HPLC, LCMS and $^1H$ NMR. Further, the reaction of mono-SNAr product 36a with aniline 7 in MeOH:TFA at 100° C. in a sealed tube for 24 h gave the desired product 60a. It was purified by column chromatography and analyzed by $^1HNMR$, LCMS and chiral analytical HPLC. The chiral analytical HPLC, LCMS and $^1H$ NMR analyses indicated that the data for the product 60a was matching with the enantiomer designated E1.

7.8.6 Cleavage of the Chiral Auxiliary From Intermediate 38b and Preparation of Stereoisomerically Pure (1S,2S 3R,4R)-N4-(3-Aminocarbonylbicyclo [2.2.1]hept-5-en-2-yl)-5-fluoro-N2-[3-methyl-4-(4methylpiperazin-1-yl)phenyl]-2,4-pyrimidinediamine Reaction:

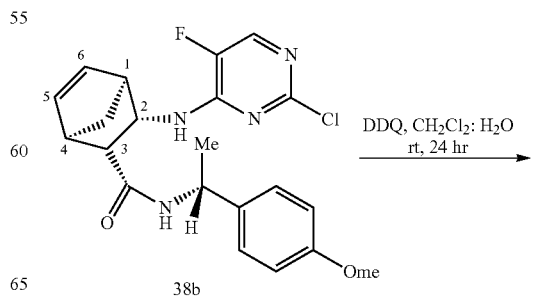

38b

-continued

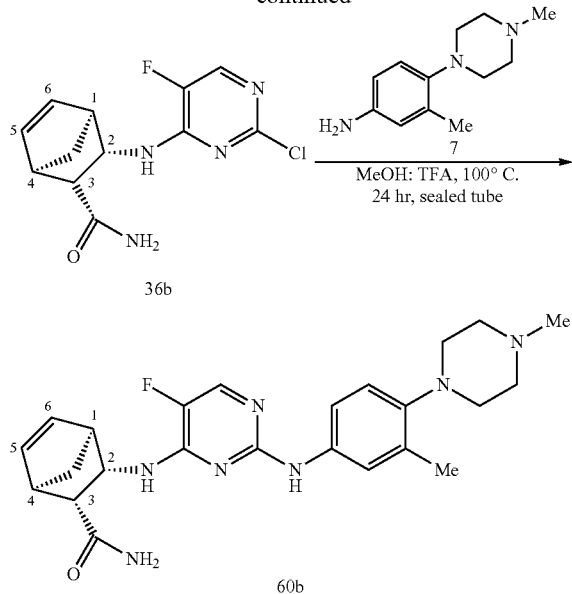

Procedure: The mono-SNAr product 38b was allowed to react with DDQ (3 equivalents) in CH$_2$Cl$_2$:H$_2$O at room temperature to obtain the desired mono-SNAr product 36b (after the cleavage of chiral auxiliary). The mono-SNAr product was purified by column chromatography and found to be a different diastereoisomer than that was obtained via enzymatic route, and this was confirmed by chiral analytical HPLC. Further, the reaction of mono-SNAr product 36b with aniline 7 in MeOH:TFA at 100° C. in a sealed tube for 24 h gave the desired product 60b. It was purified by column chromatography and analyzed by $^1$HNMR, LCMS and chiral analytical HPLC. The chiral analytical HPLC, LCMS and $^1$H NMR analyses indicated that the data for product 60b was identical with the enantiomer designed E2. $[\alpha]_D^{RT}$ –102.00° (c, 1.0 MeOH).

7.9 Preparation of HCl Salts

HCl salts of the racemate 60r1 and stereoisomerically pure 60a were prepared as described below.

7.9.1 Preparation of Racemic N4-(3-Aminocarbonylbicyclo[2.2.1]hept-5-en-2-yl)-5-fluoro-N2-[3-methyl-4-(4-methylpiperazin-1-yl)phenyl]-2,4-pyrimidinediamine Hydrogen Chloride Salt To a solution of 2-exo-3-exo racemic N4-(3-aminocarbonylbicyclo[2.2.1]hept-5-ene-2-yl)-5-fluoro-N2-[3-methyl-4-(4-methylpiperazin-1-yl)phenyl]-2,4-pyrimidinediamine (60r1) (0.140 g, 0.3 mmol) in MeOH (3 mL) at 0° C. was added HCl (4M, dioxane, 0.170 mL, 0.681 mmol) dropwise and then stirred at 0° C. for 1 h and room temperature for 15 minutes. The clear homogeneous solution was filtered, concentrated and redissolved in EtOH. Ethyl acetate was added to the ethanolic solution to precipitate the desired product, which was isolated to give 2-exo-3-exo racemic N4-(3-aminocarbonylbicyclo[2.2.1]hept-5-ene-2-yl)-5-fluoro-N2-[3-methyl-4-(4-methylpiperazin-1-yl)phenyl]-2,4-pyrimidinediamine bis hydrogen chloride salt (compound 60r1.2HCl). LCMS: purity: 98%; MS (m/e): 453 (MH$^+$).

7.9.2 Preparation of Stereoisomerically pure (1R,2R,3S,4S)-N4-(3-Aminocarbonylbicyclo[2.2.1]hept-5-en-2-yl)-5-fluoro-N2-[3-methyl-4-(4methylpiperazin-1-yl)phenyl]-2,4-pyrimidinediamine Hydrogen Chloride Salt In a like manner, supra, the interaction of 2 equivalents of HCl (4M, dioxane) with stereoisomerically pure (1R,2R,3S,4S)-N4-(3-aminocarbonylbicyclo[2.2.1]hept-5-ene-2-yl)-5-fluoro-N2-[3-methyl-4-(4-methylpiperazin-1-yl)phenyl]-2,4-pyrimidinediamine (60a) gave stereoisomerically pure (1R,2R,3S,4S)-N4-(3-aminocarbonylbicyclo[2.2.1]hept-5-ene-2-yl)-5-fluoro-N2-[3-methyl-4-(4-methylpiperazin-1-yl)phenyl]-2,4-pyrimidinediamine bis hydogen chloride salt (compound 60a.2HCl). LCMS: purity: 97%; MS (m/e): 453 (MH$^+$); $[\alpha]_D$ +46.30 (c, 0.04 MeOH).

7.10 Preparation of (1R,2R,3S,4S) N4-(3-Aminocarbonylbicyclo[2.2.1]hept-5-ene-2-yl)-5-fluoro-N2-[3-(1,3-oxazol-2-yl)phenyl]-2,4-pyrimidinediamine

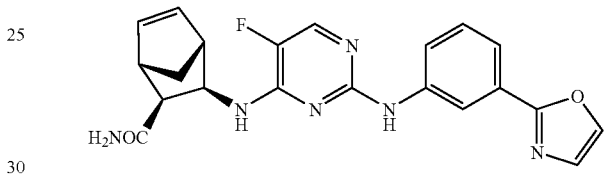

(1R,2R,3S,4S) N4-(3-aminocarbonylbicyclo[2.2.1]hept-5-ene-2-yl)-5-fluoro-N2-[3-(1,3-oxazol-2-yl)phenyl]-2,4-pyrimidinediamine (Compound 90a) was prepared as described above.

$^1$H NMR (DMSO-d6): 9.36 (s, 1H), 8.48 (s, 1H), 8.14 (s, 1H), 9.92 (d, 1H, J=3 Hz), 7.79 (d, 1H, J=7.8 Hz), 7.68 (s, 1H), 7.42 (m, 4H), 7.18 (s, 1H), 6.29 (m, 1H), 6.13 (m, 1H), 4.21 (t, 1H, J=4.8 Hz), 2.86 (s, 1H), 2.77 (s, 1H), 2.55 (d, 1H, J=8.1 Hz), 2.14 (d, 1H, J=8.4Hz), 1.39 (d, 1H, J=8.7 Hz); LCMS: purity: 98%, MS (m/e): 407 (MH$^+$).

7.11 Inhibition of Cellular Proliferation In Vitro

Compounds 60r1, 60r2, 60r1.2HCl, 60a, 60b and 60a.HCl were tested against a variety of different types of tumor cells for their ability to inhibit proliferation using standard in vitro antiproliferation assays. The various cells lines tested included: A549 (lung carcinoma); ASPC-1 (pancreatic adenocarcinoma); BXPC-3 (pabcreatic adenocarcinoma); CaOV-3 (ovarian adenocarcinoma); COLO 205 (colorectal adenocarcinoma); DU145 (prostate carcinoma); ES-2 (ovarian clear cell carcinoma); H1299 (non-small cell lung carcinoma); H1155 (non-small cell lung carcinoma); H460 (large cell lung carcinoma); HELA (cervical adenocarcinoma); HL160 (promyeloblast promyelocytic leukemia); K562 (bone marrow chronic myelogenous leukemia); L1210 (mouse lymphocytic leukemia); MiaPaCa-2 (pancreatice carcinoma); MOLT4 (T lymphoblast acute lymphoblastic leukemia); OVCAR-3 (ovarian adenocarcinoma); MOLT3 (T lymphoblast acute lymphoblastic leukemia); OVCAR-8 (ovarian carcinoma); PC3 (prostate adenocarcinoma); SK-OV-3 (ovarian adenocarcinoma); SU86.86 (pancreatic carcinoma); SW620 (colorectal adenocarcinoma); THP-1 (monocyte acute monocytic leukemia); TOV-21G (ovarian clear cell carcinoma); U2OS (bone osteosarcoma); and U937 (histiocytic lymphoma).

The $IC_{50}$ values obtained with the compounds are provided in TABLE 2, below. In TABLE 2, a "+" indicates an $IC_{50}$ value of ≤1 μM, a "++" indicates an $IC_{50}$ value of ≤20 nM, "+++" indicates an $IC_{50}$ value of ≤10 nM, and a "−" indicates an $IC_{50}$ value of >1 μM. A blank indicates that the compound was not tested against the specific cell line.

TABLE 2

In Vitro $IC_{50}$ Values of Selected Compounds

| | 60r1 | 60r1 · 2HCl | 60r2 | 60a | 60a · 2HCl | 60b |
|---|---|---|---|---|---|---|
| A549 | ++ | + | + | +++ | +++ | −− |
| ASPC1 | ++ | | | +++ | | |
| BxPC-3 | | | | +++ | | |
| CaOV-3 | | | | +++ | | |
| Colo205 | +++ | | | +++ | +++ | −− |
| DU145 | ++ | | | ++ | + | + |
| ES-2 | | | | | | |
| H1299 | | + | | +++ | + | −− |
| H1155 | +++ | | | +++ | | |
| H460 | | | | +++ | | |
| H7299 | ++ | + | + | ++ | + | −− |
| HELA | +++ | | | +++ | +++ | −− |
| HL160 | +++ | | | +++ | | −− |
| K562 | + | | | + | | −− |
| L1210 | + | | | ++ | | −− |
| Miapaca2 | +++ | | | +++ | +++ | −− |
| MOLT3 | +++ | | | +++ | | −− |
| MOLT4 | +++ | | | +++ | | −− |
| OVCAR-3 | | | | | | |
| OVCAR-8 | | | | | | |
| PC3 | ++ | | | +++ | | −− |
| SKOV3 | | | | ++ | | |
| Su86.86 | | | | ++ | | |
| SW620 | + | | | ++ | | −− |
| THP-1 | + | | | + | | + |
| TOV-G21 | | | | +++ | | |
| U20S | ++ | | | +++ | | + |
| U937 | | | | +++ | | −− |

7.12 Inhibition of Aurora Kinases in Functional Cellular Assays

Compounds 60a and 60b were tested for their ability to inhibit Aurora kinase-B in a functional cellular assay involving phosphorylation of its substrate, histone H3. For the assay, A549 cells were seeded into the wells of a microtiter tray (5000 cells/well in 100 μl F12K media) late in the afternoon on Day 1. The cells were grown overnight (37° C., 5% $CO_2$). On Day 2, 50 μl nocodazole (1 μM in media) was added to each well, giving a final concentration of 333 nM. Cells were grown for an additional 18 hrs under the same conditions.

On Day 3, 50 μl aliquots of varying concentrations of test compound were added to the wells. Test compounds were prepared by 2-fold serial dilution of a 2mM stock (in DMSO). The diluted compounds in DMSO were then further diluted 1:50 with media to yield a final solution containing 4× test compound, 98% media, 2% DMSO. After incubation, the media/test compound was washed and the cells fixed with 2% para-formaldehyde (in Dulbecco's phosphate buffered saline "DPBS"; 25 μl per well; >20 mm incubation). The fixed cells were washed once with DPBS (200 μl/well), stained with phospho-Histone H3 (Cell Signaling Technology; 1:500 in DPBS, 10% normal goat serum "NGS", 0.05% Triton X-100; 1-2 hrs at room temperature), and washed twice with DPBS (200 μl/well). The cells were then stained with a secondary antibody labeled with a fluorescent dye (secondary antibody donkey anti-mouse AlexFluor 488 (Invitrogen Molecular Probes; 1:2000) and DAPI (1:15,000 of 1 mg/ml stock) for 1 hr at room temperature, washed three times with DPBS (200 μl/well) and stored under DPBS (100 μl/well) at 4° C. until ready for analysis.

A Zeiss Axiovert S100 inverted fluorescent microscope with a Plan-NEOFLUAR 10× objective, a Hamamatsu Lightningcure 200 Mercury-Xenon light source and an Omega Optical XF57 quad filter was used for all data collection. The system was equipped with a Ludl Mac2000 motorized stage with X/Y/Z control, a Ludl filter wheel, a Zymark Twister robot arm and a Quantix digital camera from Roper Scientific. All hardware was controlled with ImagePro 4.5 with the ScopePro/StagePro 4.1 module (Media Cybernetics) on a PC running Win2000. Visual Basic Scripts were written for ImagePro to automate hardware control and image collection. Focusing was performed with a software auto-focus routine contained with StagePro that used the maximum local contrast to determine the best plane of focus from a Z series captured once in each well. Once proper focus was achieved images were captured in a 3×3 grid pattern of adjacent images next to, but not including, the position of focusing. Images were captured and analyzed in 12-bit format using segmentation and morphological routines contained in the Image Pro software package. Identified nuclei were counted and pixel data for each cell along with experimental conditions was stored in a database using MYSQL 4.0.14. Subsequent analysis of experimental results and graph creation was done using Matlab 6.5.

For phospho-histone H3 analysis the data is converted to Facs files and analysed using FlowJo. The percent Phospho-H3 cells are plotted at each compound concentration to determine an EC50 for Aurora B inhibition.

Results. Compound 60a inhibited Aurora kinase-B with an $IC_{50}$ of about 7 nM in this assay. By contrast, the $IC_{50}$ of its enantiomer, compound 60b, was 2.49 μM, approx. 350 times greater.

7.13 Pharmacokinetics of Compound E1 in Monkeys

Compound 60a was administered to monkeys intraveinously (1 mg/kg in saline) and orally (5 mg/kg in saline) and the plasma concentrations monitored over time. When administered by i.v., the plasma concentration of compound remained above the $IC_{50}$ of 7 nM for 11 hrs following administration; when administered orally, a plasma concentration of compound above the $IC_{50}$ was maintained for over 20 hrs.

7.14 Compound 60a Shrinks Tumors In Vivo

Compound 60a.2HCl, was tested for its ability to shrink A549 and Colo205 tumors in a standard xenograft therapeutic model in SCID mice, and Colo205 and MiaPaCa tumors in a standard xenograph regression model in SCID mice. When palpable tumors appeared and were of a preselected volume (approx. 100 mm3 for treatment model; >300 mm3 for regression model), the mice were administered test compounds in the amounts and according to the dosing regimens specified in TABLE 3 (treatment protocol) and TABLE 4 (regression protocol), below.

TABLE 3

Summary of Treatment Model Experiments
(Mean tumor size 100 mm³)

| Cell Line | Dose (mg/kg/day) | Schedule (day on/day off) | Route |
|---|---|---|---|
| Colo205 | 2 | 4/3 | oral |
| Colo205 | 10 | 4/3 | oral |
| Colo205 | 10 | 2/1 | oral |
| Colo205 | 10 | 5/2 | oral |
| Colo205 | 10 | 7/7 | oral |
| Colo205 | 10 | 3/11 | oral |
| Colo205 | 10 | 1/6 | oral |
| Colo205 | 10 | daily | oral |
| A549 | 10 | 5/2 | oral |
| A549 | 10 | 2/1 | oral |
| A549 | 10 | 7/7 | oral |
| A549 | 10 | daily (13 days) | i.p. |
| A549 | 20 | daily (5 days) | i.p. |

TABLE 4

Summary of Progression Model Experiments
(Mean tumor size >300 mm³)

| Cell Line | Dose (mg/kg/day) | Schedule | Route |
|---|---|---|---|
| Colo205 | 10 | daily (13 days) | oral |
| MiaPaCa | 10 | daily (3 cycles) | oral |
| MiaPaCa | 10 | daily (3 cycles) | i.p. |

Figure 2:
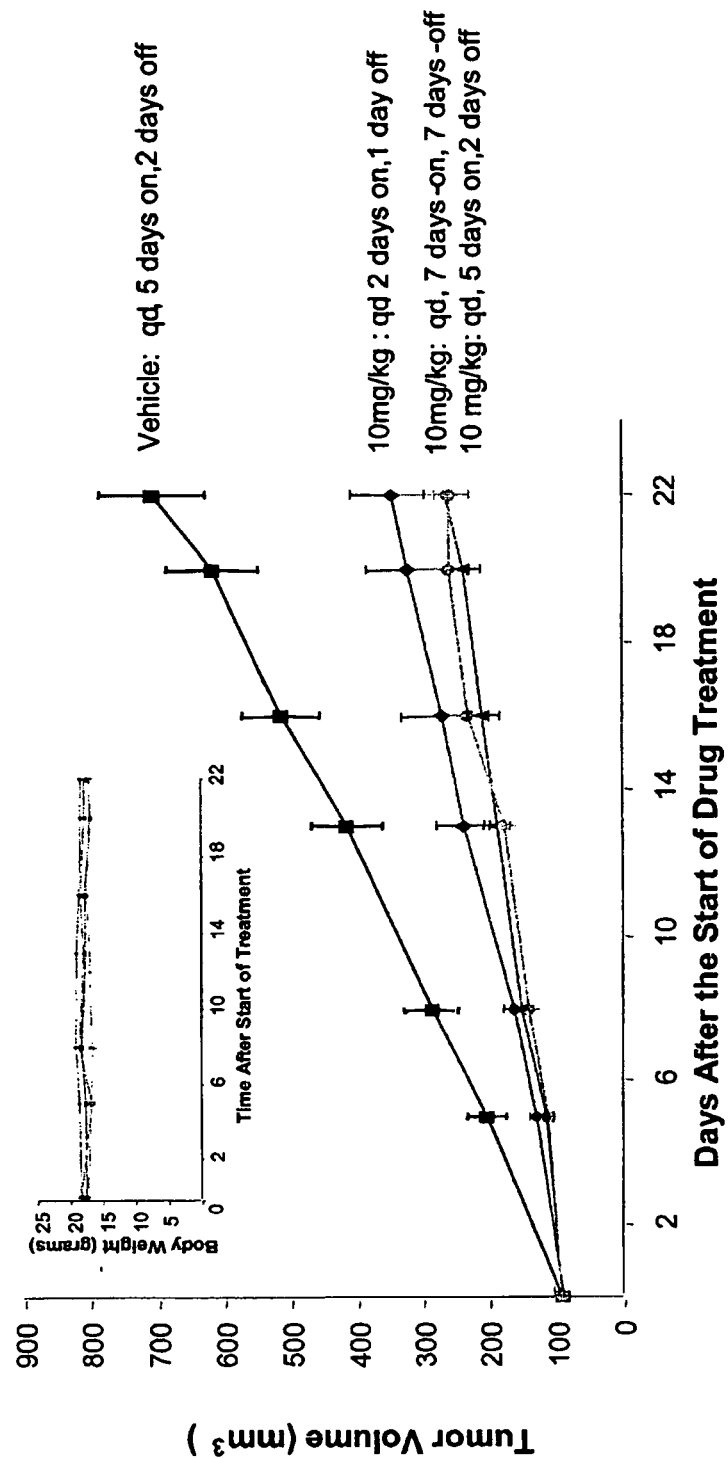

Results. The inhibitory effects of Compound 60a.2HCl on Colo205 tumor growth in the treatment model are illustrated in FIGS. 1 and 2. The results of the daily dosing regimen are illustrated in FIG. 1; the results of the pulsed dosing regimens in FIG. 2. Both dosing regimens yielded significant ($p<0.050$) reductions in tumor growth rate as compared to a vehicle control for all dosage levels tested. A 549 tumors were less responsive to treatment resulting in an approximate 40% reduction in mean tumor volume following a dosing regimen of 5 days on/2 days off and a dose level of 10 mg/kg qd ($p>0.05$).

Figure 3:
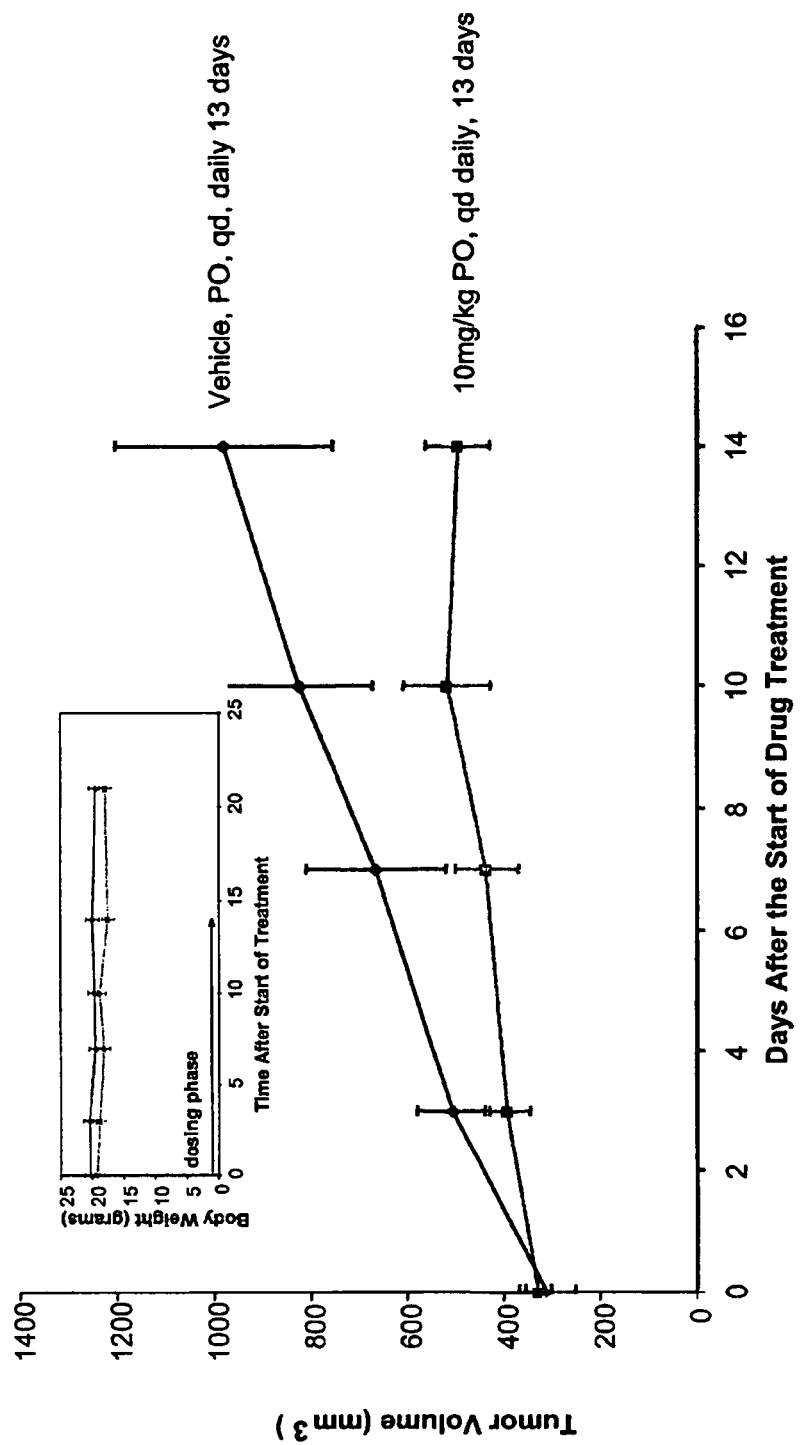
Figure 4:
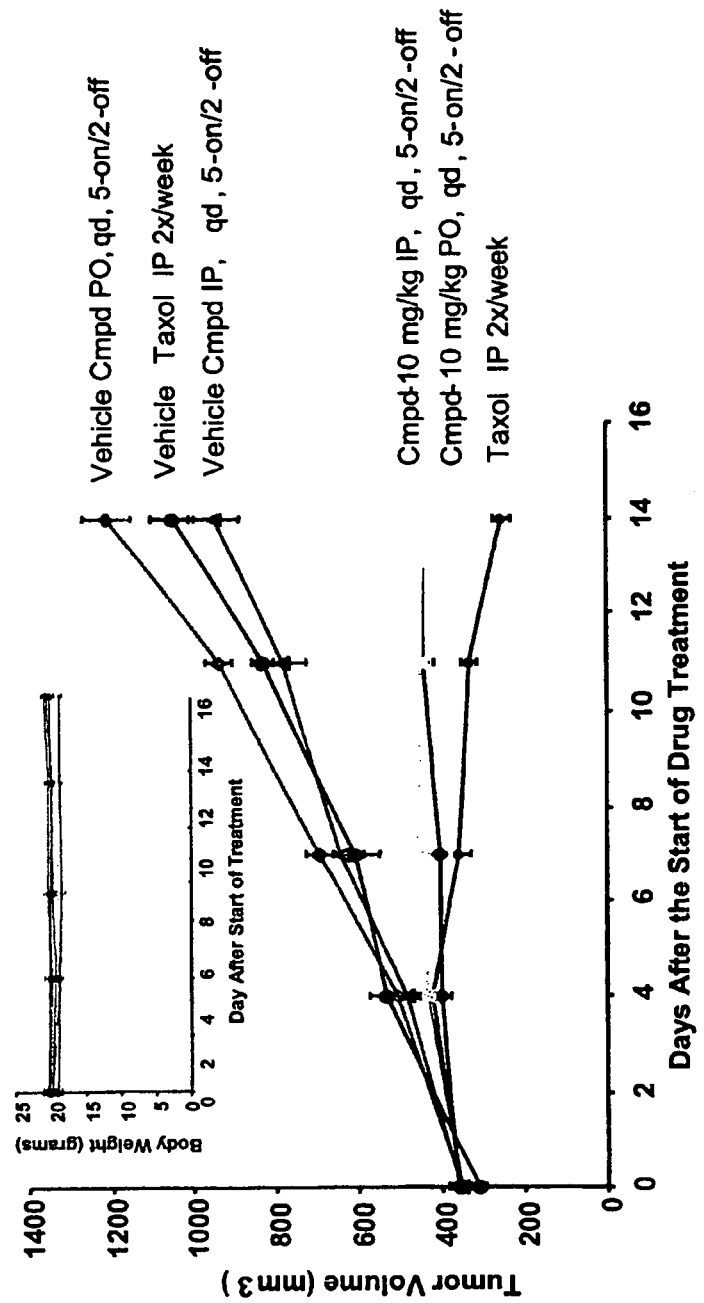

The inhibitory effects of Compound 60a.2HCl on Colo205 tumor growth in the regression model are illustrated in FIG. 3. The effects of Compound 60a.2HCl on MiaPaCa tumors in the regression model are illustrated in FIG. 4. Significant reductions in tumor growth rate were observed with both tumor lines. These reductions were independent of the mode of administration. Moreover, the reductions observed in MiaPaCa tumors were similar to those observed with taxol (see FIG. 4).

Although the foregoing inventions have been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

All literature and patent references cited throughout the application are incorporated into the application by reference for all purposes.

What is claimed is:

1. A compound that is (1R,2R,3S,4S)—N4-(3-aminocarbonylbicyclo [2.2.1]hept-5-ene-2-yl)-5-fluoro-N2-[3-methyl-4-(4-methylpiperazin-1-yl)]phenyl-2,4-pyrimidinediamine or a pharmaceutically acceptable salt thereof.

2. A composition comprising N4-(3-aminocarbonylbicyclo[2.2.1]hept-5-ene-2-yl)-5-fluoro-N2-[3-methyl-4-(4-methylpiperazin-1-yl)]phenyl-2,4-pyrimidinediamine or salt thereof and a pharmaceutically acceptable carrier, excipient, and/or diluent, wherein the composition is enriched in the (1R,2R,3S,4S)-diastereomer.

3. A composition comprising a compound according to claim 1 and a pharmaceutically acceptable carrier, excipient, and/or diluent.

* * * * *